US008889720B2

(12) United States Patent
Bachovchin et al.

(10) Patent No.: US 8,889,720 B2
(45) Date of Patent: Nov. 18, 2014

(54) NON-FLUSHING NIACIN ANALOGUES, AND METHODS OF USE THEREOF

(71) Applicant: Trustees of Tufts College, Boston, MA (US)

(72) Inventors: William W. Bachovchin, Cambridge, MA (US); Hung-sen Lai, Andover, MA (US)

(73) Assignee: Trustees of Tufts College, Boston, MA (US)

( * ) Notice: Subject to any disclaimer, the term of this patent is extended or adjusted under 35 U.S.C. 154(b) by 49 days.

(21) Appl. No.: 13/715,242

(22) Filed: Dec. 14, 2012

(65) Prior Publication Data

US 2013/0217714 A1   Aug. 22, 2013

Related U.S. Application Data

(63) Continuation of application No. 12/376,238, filed as application No. PCT/US2007/074960 on Aug. 1, 2007, now Pat. No. 8,377,971.

(60) Provisional application No. 60/835,194, filed on Aug. 3, 2006.

(51) Int. Cl.
| | |
|---|---|
| *C07D 213/02* | (2006.01) |
| *C07D 401/06* | (2006.01) |
| *A61K 31/44* | (2006.01) |
| *A61K 31/4439* | (2006.01) |
| *C07D 213/80* | (2006.01) |
| *A61K 45/06* | (2006.01) |
| *C07D 213/55* | (2006.01) |

(52) U.S. Cl.
CPC .......... *A61K 31/4439* (2013.01); *C07D 213/80* (2013.01); *A61K 45/06* (2013.01); *C07D 401/06* (2013.01); *C07D 213/55* (2013.01)
USPC .......... 514/356; 514/340; 546/268.1; 546/318

(58) Field of Classification Search
None
See application file for complete search history.

(56) References Cited

U.S. PATENT DOCUMENTS

| | | | |
|---|---|---|---|
| 4,388,317 | A | 6/1983 | Brown |
| 4,444,775 | A | 4/1984 | Ford |
| 5,352,684 | A | 10/1994 | Zimmermann et al. |
| 6,462,047 | B1 | 10/2002 | Bombrun et al. |
| 2005/0222151 | A1 | 10/2005 | Carruthers et al. |

FOREIGN PATENT DOCUMENTS

| | | |
|---|---|---|
| EP | 0013153 A1 | 7/1980 |
| EP | 1445250 A1 | 8/2004 |
| JP | 2006/056884 A | 3/2006 |
| JP | 2009/520851 A | 5/2009 |
| JP | 2009/544616 A | 12/2009 |
| WO | WO-00/15639 A1 | 3/2000 |
| WO | WO-03/028724 A1 | 4/2003 |
| WO | WO-2006/121719 A2 | 11/2006 |
| WO | WO-2006/122011 A2 | 11/2006 |

OTHER PUBLICATIONS

Isoda, S. et al., "Medicinal Chemical Studies on Antiplasmin Drugs. VI. Aza Analogs of 4-Aminomethylbenzoic Acid," *Chemical and Pharmaceutical Bulletin, Pharmaceutical Society of Japan* 28(5): 1408-1414 (1980).
Kato, K. et al., "Thromboxane Synthetase Inhibitors (TXSI). Design, Synthesis and Evaluation of a Novel Series of ω-Pyridylalkenoic Acids," *Journal of Medicinal Chemistry,* 28(3): 287-294 (1985).
Moradei, O et al., "Substituted N-(2-aminophenyl)-benzamides, (E)-N-(2-aminophenyl)-acrylamides and Their Analogues: Novel Classes of Histone Deacetylase Inhibitors," *Bioorganic Medicinal Chemistry Letters* 16:4048-4052 (2006).
Schobert, R. et al., "cis-Dicloroplatinum (II) complexes with aminomethylnicotinate and—isonicotinate ligands," *Inorganica Chimica Acta,* 358(12): 3369-3376 (2005).
Scopes, D. et al., "New Kappa Receptor Agonists Based Upon a 2-[(alkylamino)methyl]piperidine Nucleus," *Journal of Medicinal Chemistry* 35(3): 490-501 (1992).
International Search Report for PCT/US07/74960 mailed Sep. 22, 2008.
Office Action from corresponding Mexican application No. MX/a/2009/001279 dated Apr. 1, 2013.
Office Action from corresponding Japanese application No. 2009-523035 dated Oct. 16, 2012.
Supplementary European Search Report for European Patent Application No. 07 79 9967 dated Feb. 10, 2010.

*Primary Examiner* — Zinna Northington Davis
(74) *Attorney, Agent, or Firm* — Dana M. Gordon; Foley Hoag LLP

(57) ABSTRACT

One aspect of the present invention relates to substituted pyridines and pharmaceutically acceptable salts thereof that are active against a range of mammalian maladies. Another aspect of the invention relates to a pharmaceutical composition, comprising a compound of the present invention or a pharmaceutically acceptable salt thereof; and a pharmaceutically acceptable excipient. The present invention also relates to methods of treating a range of mammalian maladies or conditions, including but not limited to hyperlipidemia, hypercholesterolemia, atherosclerosis, coronary artery disease, congestive heart failure, cardiovascular disease, hypertension, coronary heart disease, angina, pellagra, Hartnup's syndrome, carcinoid syndrome, arterial occlusive disease, obesity, hypothyroidism, vasoconstriction, osteoarthritis, rheumatoid arthritis, diabetes, Alzheimer's disease, lipodystrophy, or dyslipidemia, raising serum high-density lipoprotein (HDL) levels, and lowering serum low-density lipoprotein (LDL) levels.

34 Claims, 3 Drawing Sheets

Figure 2

Comparative Analysis of Effect of Niacin Analogs on PGD2 Release and HDL uptake

| KOS ID | PGD2 release - Flushing (% Niacin) | HDL Uptake inhibition (% Control) |
|---|---|---|
| Niacin | 100 | 18.7 |
| 2035 | 34 | 12.7 |
| 2037 | 218 | No effect |
| 2038 | 108 | No effect |
| 2040 | 167 | No effect |
| 2230A | 126 | No effect |
| 2230B | 141 | No effect |
| 2230C | 91 | 30.4 |

NON-FLUSHING NIACIN ANALOGUES, AND METHODS OF USE THEREOF

RELATED APPLICATIONS

This application is a continuation of U.S. patent application Ser. No. 12/376,238, now U.S. Pat. No. 8,377,971, filed Feb. 3, 2009; which is a national stage application under 35.U.S.C. 371 based on Patent Cooperation Treaty Application serial number PCT/US2007/074960, filed Aug. 1, 2007; which claims the benefit of priority to U.S. Provisional Patent Application Ser. No. 60/835,194, filed Aug. 3, 2006.

BACKGROUND OF THE INVENTION

Hyperlipidemia and hypercholesterolemia are conditions that have a well established correlation with increased risk of other conditions, such as heart attacks, atherosclerosis, and other deleterious ailments. There are numerous agents available for lowering cholesterol and lipid levels, including gemfibrizol, probucol, and, more recently, the "statins" e.g., lovastatin.

Niacin (nicotinic acid and/or nicotinamide), a water soluble B-complex vitamin, is used orally for the treatment of hyperlipidemia. Niacin has been shown to be effective in reducing total plasma cholesterol (C), low density lipoproteins LDL-C and very low density lipoprotein triglycerides (VLDL-triglycerides), all of which are associated with health risks. Simultaneously, niacin raises serum levels of high density lipoproteins (HDL-C), which are considered a "healthy" lipoprotein, in patients with types II, III, IV, and V hyperlipoproteinemia.

Although the mechanism by which niacin alters lipid profiles has not been well defined, its mechanisms of action have been shown to include inhibition of free fatty acid release from adipose tissue (see Carlson, L. A., Froberg, S. O. and Nye, E. R., Nicotinic acid in the rat. 11. Acute effects of nicotinic acid on plasma, liver, heart, and muscle lipids, Acta Med Scand 180: 571-579, 1966), and increased lipoprotein lipase activity (see Priego, J. G., Pina, M., Armijo, M., Sunkel, C. and Maroto, M. L., Action of etofibrate, clofibrate and nicotinic acid on the metabolism of lipids in normolipemic rats. Short term effects and method of action, Arch Farmacol Toxicol 5: 29-42, 1979). More than 30 million Americans have elevated blood LDL-C levels. HMG-CoA reductase inhibitors (statins) are the most widely used class of drugs for treating patients with elevated levels of LDL-C. Niacin, however, is the only drug recommended by the American Heart Association for HDL improvement in primary prevention of cardiovascular diseases in addition to lowering LDL-C. Niacin therapy is not only cost-effective as a monotherapy, but it is also beneficial as a combination therapy because it complements the effects of other classes of lipid-lowering drugs. However, niacin is a second or third choice for isolated, hypercholesterolemia because of a high incidence of side effects associated with oral niacin therapy. Nevertheless, it has a therapeutic advantage as a monotherapy when reduction of both LDL-C and triglycerides are desired, such as for patients with severe combined hyperlipidemia.

Niacin may also be used in combination with other cholesterol-lowering agents, such as the "statins", to maximize lipid-lowering activity. One study showed that a niacin/lovastatin combination is highly effective in lowering LDL-C, triglycerides and lipoprotein a[Lp(a)] while retaining niacin's potency in raising HDL-C (Kashyap, M. L., Evans R., Simmons, P. D., Kohler, R. M. and McGoven, M. E., New combination niacin/statin formulation shows pronounced effects on major lipoproteins and well tolerated, J Am Coll Card Suppl. A 35: 326, 2000).

Niacin has been widely used for reducing serum cholesterol levels because it is considered a cost-effective therapy. Daily oral doses of 2-3 g niacin in humans reduce levels of total-C and LDL-C by an average of 20% to 30%, reduce triglyceride levels 35% to 55%, increase HDL-C 20% to 35%, and reduce Lp(a). Niacin also reduces total mortality as well as mortality from coronary artery disease (see The Coronary Drug Project Research Group, JAMA 231: 360-381, 1975; and Canner, P. L., Berge, K. G., Wenger, N. K., Stamler, J., Friedman, L., Prineas, R. J. and Friedewald, W., Fifteen year mortality in Coronary Drug Project patients: long-term benefit with niacin, J Am Coll Cardiol 8: 1245-1255, 1986) and it helps to slow or reverse the progression of atherosclerosis (see Blankenhorn, D. H., Nessim, S. A., Johnson, R. L., Samnarco, M. E., Azen, S. P. and Cashin-Hemphill, L., Beneficial effects of combined colestipol-niacin therapy on coronary atheroscloerosis and coronary venous bypass grafts, JAMA 257: 3233-3240, 1987; and Cashin-Hemphill L.; Mack, W. J., Pogoda, J. M., Samnarco, M. E., Azen, S. P. and Blankenhorn, D. H., Beneficial effects of colestipol-niacin on coronary atherosclerosis. A 4-year follow-up, JAMA 264: 3013-3017, 1990).

Unfortunately, oral niacin therapy has side effects that limit its utility. Although niacin is a vitamin, it must be used in therapeutic doses to lower cholesterol. At these doses, both immediate-release and sustained-release niacin can have several side effects. The most common side effect of niacin is flushing, a warm feeling in the skin usually associated with redness and sometimes itching. Flushing is not dangerous, but most patients find it very uncomfortable, which seriously limits patient compliance with niacin therapy. Niacin-induced flushing can be substantially attenuated by pretreatment with cyclooxygenase inhibitors, suggesting that the vasodilation is caused by a prostaglandin-mediated mechanism (see Carlson, L. A., Nicotinic acid and inhibition of fat mobilizing lipolysis. Present status, of effects on lipid metabolism, Adv Exp Med Biol 109: 225-23 8, 1978).

Liver function tests are always monitored in patients taking niacin since elevation of serum transaminase levels has been associated with niacin treatment, and sustained-release niacin formulations have been associated with more serious liver problems (see McKenney, J. M., Proctor, J. D., Harris, S., and Chinchili, V. M., A comparison of the efficacy and toxic effects of sustained- vs immediate-release niacin in hypercholesterolemic patients, JAMA 271: 672-777, 1994; and Stafford, R. S., Blumenthal, D. and Pasternak, R. C., Variations in cholesterol management practices of U.S. physicians, J Am Coll Cardiol 29: 139-146, 1997). Other known side effects of oral niacin therapy include activation of peptic ulcers, gout, and worsening of diabetes control. Accordingly, the safety and efficacy of oral niacin therapy is undermined by the need for careful clinical monitoring and the compound's side-effect profile.

SUMMARY OF THE INVENTION

One aspect of the present invention relates to substituted pyridines and pharmaceutically acceptable salts thereof that are active against a range of mammalian maladies. In certain embodiments, said pyridines or salts thereof comprise at the 3-position or 5-position a substituent comprising a functional group that is substantially anionic at physiological pH. In certain embodiments, said pyridines or salts thereof comprise at the 2-position or 6-position a substituent comprising a functional group that is electron donating to the pyridine ring. In certain embodiments, said pyridines or salts thereof comprise at the 5-position a substituent comprising a functional group that is substantially anionic at physiological pH; and at the 2-position a substituent comprising a functional group that is electron donating to the pyridine ring.

Another aspect of the invention relates to a pharmaceutical composition, comprising a compound of the present invention or a pharmaceutically acceptable salt thereof; and a pharmaceutically acceptable excipient. Yet another aspect of the invention relates to a pharmaceutical composition, comprising a compound of the present invention or a pharmaceutically acceptable salt thereof; niacin; and a pharmaceutically acceptable excipient. Another aspect of the invention relates to a pharmaceutical composition, comprising a compound of the present invention or a pharmaceutically acceptable salt thereof; a statin selected from the group consisting of atorvastatin, cerivastatin, fluvastatin, lovastatin, mevastatin, pitavastatin, pravastatin, rosuvastatin, simvastatin, gemcabene, and probucol; and a pharmaceutically acceptable excipient. The present invention also relates to a pharmaceutical composition, comprising a compound of the present invention or a pharmaceutically acceptable salt thereof; niacin; a statin selected from the group consisting of atorvastatin, cerivastatin, fluvastatin, lovastatin, mevastatin, pitavastatin, pravastatin, rosuvastatin, simvastatin, gemcabene, and probucol; and a pharmaceutically acceptable excipient.

The present invention also relates to a method of treating hyperlipidemia, hypercholesterolemia, atherosclerosis, coronary artery disease, congestive heart failure, cardiovascular disease, hypertension, coronary heart disease, angina, pellagra, Hartnup's syndrome, carcinoid syndrome, arterial occlusive disease, obesity, hypothyroidism, vasoconstriction, osteoarthritis, rheumatoid arthritis, diabetes, Alzheimer's disease, lipodystrophy, or dyslipidemia, comprising the step of administering to a mammal in need thereof a therapeutically effective amount of a compound or pharmaceutical composition of the present invention. Another aspect of the present invention relates to a method of raising serum high-density lipoprotein (HDL) levels, comprising the step of administering to a mammal in need thereof a therapeutically effective amount of a compound or pharmaceutical composition of the present invention. Yet another aspect of the present invention relates to a method of lowering serum low-density lipoprotein (LDL) levels, comprising the step of administering to a mammal in need thereof a therapeutically effective amount of a compound or pharmaceutical composition of the present invention.

BRIEF DESCRIPTION OF THE FIGURES

FIG. 2 tabulates the effects of various niacin analogues of the present invention on PGD2 release and inhibition of HDL uptake.

DETAILED DESCRIPTION OF THE INVENTION

The invention will now be described more fully with reference to the accompanying examples, in which certain preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Overview

One aspect of the invention relates to niacin analogues for use in raising serum HDL levels in mammals. The compounds of the invention have equal or greater HDL-raising ability than niacin while having less or no propensity to induce flushing, an undesirable side effect of niacin itself when used in doses sufficient to raise serum HDL levels. In certain embodiments, key structural features appear to include the placement of a negatively charged group at a greater distance from the pyridine ring in a sterically constrained trans configuration relative to the ring and/or the absence of a carbonyl oxygen in the position analogous to that occupied by the carboxyl group in niacin.

Figure 1:
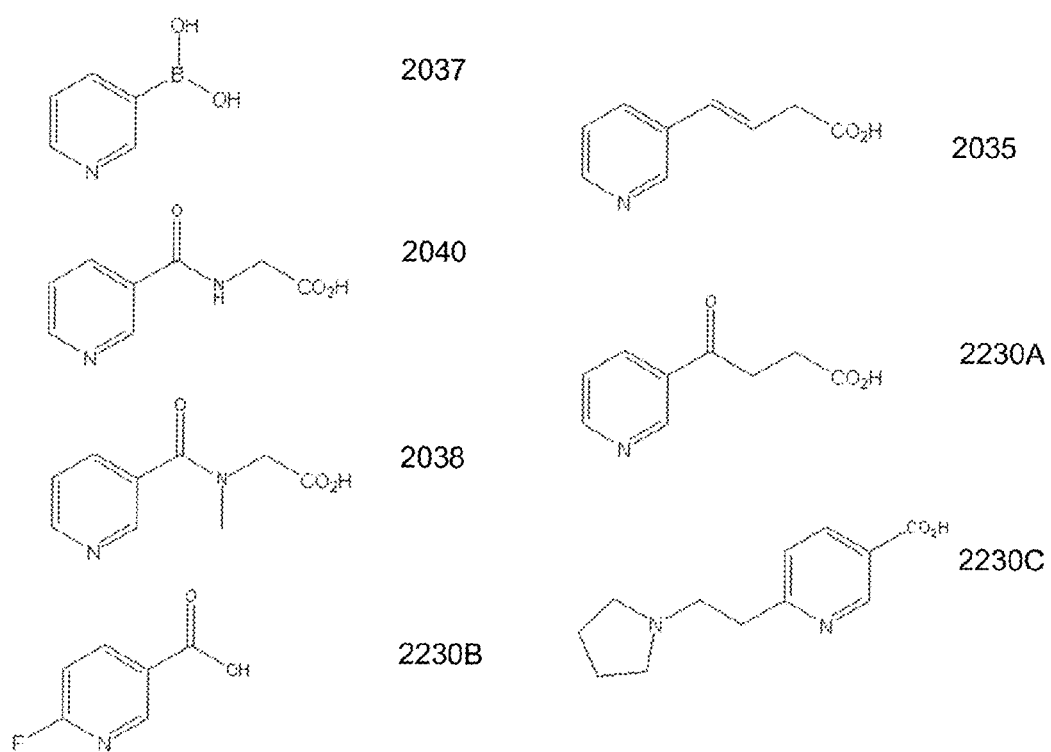
FIG. 1 depicts various niacin analogues of the present invention.
Figure 3:
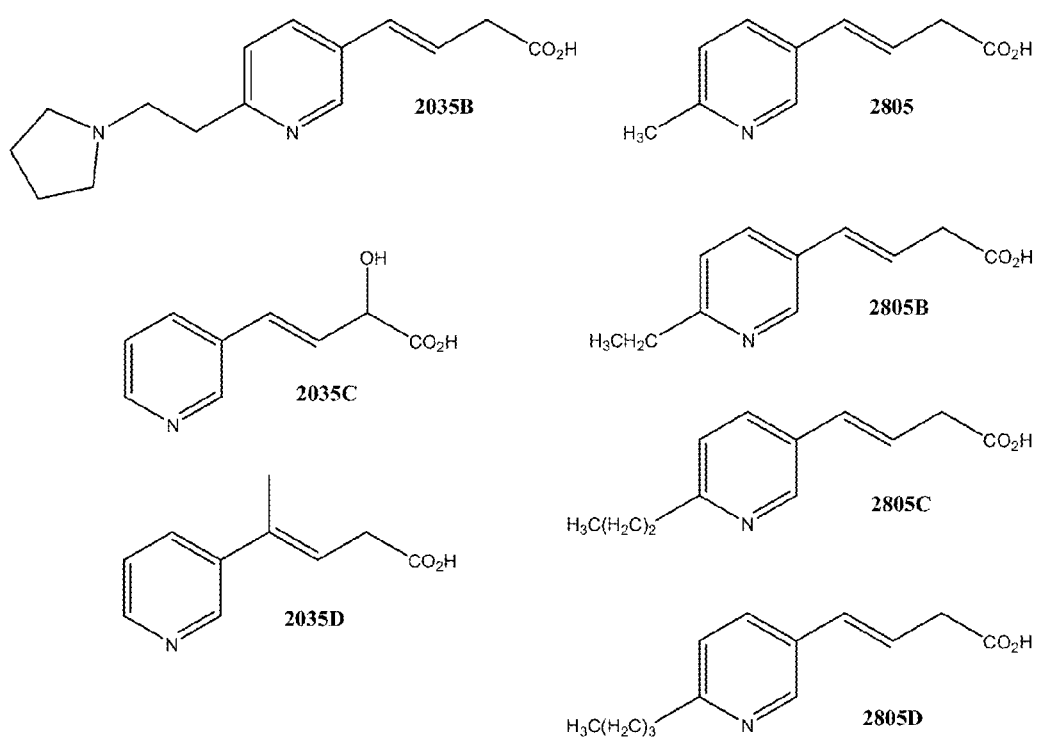
FIG. 3 depicts various niacin analogues of the present invention.

For example, 4-pyridin-3-yl-but-3-enoic acid (2035) reduces HDL uptake by Hep-G2 cells, which is an assay that serves as proxy for HDL-raising activity, essentially as well as niacin and yet has very much less ability to induce PDG2 release by THP-1 macrophages, which is an assay that serves as proxy for flush inducing activity (FIG. 1 and Table 1) while the structurally very similar compounds, 2040, 2038, and 2230A (FIG. 1) have no HDL-raising activity, yet are more potent that niacin itself in inducing flushing (Table 1). The results also indicate that the HDL-raising activity niacin and therefore of niacin analogs like 2235 can be improved by substitutions to the niacin ring in the position para to the carboxylate group as illustrated by 2230C (FIG. 1, and Table 1). 2030C is niacin with a substitution para to the carboxylate group. The results in Table 1 show this molecule is better than niacin itself in raising HDL. However it retains the ability to generate flush. We propose that an improved niacin analog can be constructed that has greater HDL-raising activity than niacin and greatly reduced propensity to generate flush by adding substitutent in the para position of 2230C to 2035.

Compounds of the Invention

In certain embodiments, the present invention relates to a compound represented by structure A, or a pharmaceutically acceptable salt thereof:

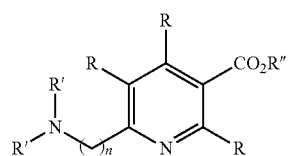

wherein

R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl;

R' represents independently for each occurrence H, alkyl, alkenyl, alkynyl, aryl, heteroaryl, aralkyl, heteroaralkyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, formyl, acyl, amino, alkylamino, arylamino, heteroarylamino, aralkylamino, heteroaralkylamino, alkenylamino, alkynylamino, formylamino, acylamino, alkyloxycarbonyl, aryloxycarbonyl, heteroaryloxycarbonyl, aralkyloxycarbonyl, heteroaralkyloxycarbonyl, alkylaminocarbonyl, arylaminocarbonyl, heteroarylaminocarbonyl, aralkylaminocarbonyl, or heteroaralkylaminocarbonyl; or the two instances of R' taken together represent —(CH$_2$)$_2$—; —(CH$_2$)$_3$—, —(CH$_2$)$_4$—, —(CH$_2$)$_5$—, or —(CH$_2$)$_6$;

R" represents independently for each occurrence H, alkyl, alkenyl, alkynyl, aryl, heteroaryl, aralkyl, or heteroaralkyl; and n is 1, 2, 3, or 4.

In certain embodiments, the present invention relates to any of the aforementioned compounds represented by structure A or the pharmaceutically acceptable salts thereof and the attendant limitations, wherein R represents independently for each occurrence H, alkyl, fluoride, chloride, bromide, nitro, cyano, sulfonic acid, hydroxyl, alkoxyl, thiol, alkylthio, formyl, acyl, formyloxy, acyloxy, formylthio, acylthio, amino, alkylamino, formylamino, acylamino, or carboxylate.

In certain embodiments, the present invention relates to any of the aforementioned compounds represented by structure A or the pharmaceutically acceptable salts thereof and the attendant limitations, wherein R represents independently for each occurrence H, or alkyl.

In certain embodiments, the present invention relates to any of the aforementioned compounds represented by structure A or the pharmaceutically acceptable salts thereof and the attendant limitations, wherein R represents independently for each occurrence H.

In certain embodiments, the present invention relates to any of the aforementioned compounds represented by structure A or the pharmaceutically acceptable salts thereof and the attendant limitations, wherein R' represents independently for each occurrence H, alkyl, alkenyl, alkynyl, aryl, heteroaryl, aralkyl, or heteroaralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure A or the pharmaceutically acceptable salts thereof and the attendant limitations, wherein R' represents independently for each occurrence H, alkyl, or aralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure A or the pharmaceutically acceptable salts thereof and the attendant limitations, wherein the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure A or the pharmaceutically acceptable salts thereof and the attendant limitations, wherein the two instances of R' taken together represent —(CH$_2$)$_4$—.

In certain embodiments, the present invention relates to any of the aforementioned compounds represented by structure A or the pharmaceutically acceptable salts thereof and the attendant limitations, wherein R" represents H or alkyl.

In certain embodiments, the present invention relates to any of the aforementioned compounds represented by structure A or the pharmaceutically acceptable salts thereof and the attendant limitations, wherein R" represents H.

In certain embodiments, the present invention relates to any of the aforementioned compounds represented by structure A or the pharmaceutically acceptable salts thereof and the attendant limitations, wherein n is 2.

In certain embodiments, the present invention relates to any of the aforementioned compounds represented by structure A or the pharmaceutically acceptable salts thereof and the attendant limitations, wherein R represents independently for each occurrence H; and n is 2.

In certain embodiments, the present invention relates to any of the aforementioned compounds represented by structure A or the pharmaceutically acceptable salts thereof and the attendant limitations, wherein R represents independently for each occurrence H; and the two instances of R' taken together represent —(CH$_2$)$_4$—.

In certain embodiments, the present invention relates to any of the aforementioned compounds represented by structure A or the pharmaceutically acceptable salts thereof and the attendant limitations, wherein R represents independently for each occurrence H; the two instances of R' taken together represent —(CH$_2$)$_4$—; and n is 2.

In certain embodiments, the present invention relates to any of the aforementioned compounds represented by structure A or the pharmaceutically acceptable salts thereof and the attendant limitations, wherein R represents independently for each occurrence H; and R" represents H or alkyl.

In certain embodiments, the present invention relates to any of the aforementioned compounds represented by structure A or the pharmaceutically acceptable salts thereof and the attendant limitations, wherein R represents independently for each occurrence H; R" represents H or alkyl; and n is 2.

In certain embodiments, the present invention relates to any of the aforementioned compounds represented by structure A or the pharmaceutically acceptable salts thereof and the attendant limitations, wherein R represents independently for each occurrence H, or alkyl; R' represents independently for each occurrence H, alkyl, alkenyl, alkynyl, aryl, heteroaryl, aralkyl, or heteroaralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—; and R" represents H or alkyl.

In certain embodiments, the present invention relates to any of the aforementioned compounds represented by structure A or the pharmaceutically acceptable salts thereof and the attendant limitations, wherein R represents independently for each occurrence H, or alkyl; the two instances of R' taken together represent —(CH$_2$)$_4$—; and R" represents H or alkyl.

In certain embodiments, the present invention relates to any of the aforementioned compounds represented by structure A or the pharmaceutically acceptable salts thereof and the attendant limitations, wherein R represents independently for each occurrence H; the two instances of R' taken together represent —(CH$_2$)$_4$—; and R" represents H or alkyl.

In certain embodiments, the present invention relates to any of the aforementioned compounds represented by structure A or the pharmaceutically acceptable salts thereof and the attendant limitations, wherein R represents independently for each occurrence H; the two instances of R' taken together represent —(CH$_2$)$_4$—; R" represents H or alkyl; and n is 2.

In certain embodiments, the present invention relates to any of the aforementioned compounds represented by structure A or the pharmaceutically acceptable salts thereof and the attendant limitations, wherein R represents independently for each occurrence H; the two instances of R' taken together represent —(CH$_2$)$_4$—; R" represents H; and n is 2.

In certain embodiments, the present invention relates to a compound represented by structure B, or a pharmaceutically acceptable salt thereof:

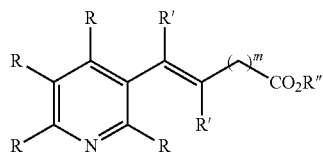

B wherein

R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl;

R' represents independently for each occurrence H, alkyl, alkenyl, alkynyl, aryl, heteroaryl, aralkyl, or heteroaralkyl;

R" represents independently for each occurrence H, alkyl, alkenyl, alkynyl, aryl, heteroaryl, aralkyl, or heteroaralkyl; and m is 1, 2, or 3.

In certain embodiments, the present invention relates to any of the aforementioned compounds represented by structure B or the pharmaceutically acceptable salts thereof and the attendant limitations, wherein R represents independently for each occurrence H, alkyl, fluoride, chloride, bromide, nitro, cyano, sulfonic acid, hydroxyl, alkoxyl, thiol, alkylthio, formyl, acyl, formyloxy, acyloxy, formylthio, acylthio, amino, alkylamino, formylamino, acylamino, or carboxylate.

In certain embodiments, the present invention relates to any of the aforementioned compounds represented by structure B or the pharmaceutically acceptable salts thereof and the attendant limitations, wherein R represents independently for each occurrence H, or alkyl.

In certain embodiments, the present invention relates to any of the aforementioned compounds represented by structure B or the pharmaceutically acceptable salts thereof and the attendant limitations, wherein R represents independently for each occurrence H.

In certain embodiments, the present invention relates to any of the aforementioned compounds represented by structure B or the pharmaceutically acceptable salts thereof and the attendant limitations, wherein R' represents independently for each occurrence H or alkyl.

In certain embodiments, the present invention relates to any of the aforementioned compounds represented by structure B or the pharmaceutically acceptable salts thereof and the attendant limitations, wherein R' represents independently for each occurrence H.

In certain embodiments, the present invention relates to any of the aforementioned compounds represented by structure B or the pharmaceutically acceptable salts thereof and the attendant limitations, wherein R" represents H or alkyl.

In certain embodiments, the present invention relates to any of the aforementioned compounds represented by structure B or the pharmaceutically acceptable salts thereof and the attendant limitations, wherein R" represents H.

In certain embodiments, the present invention relates to any of the aforementioned compounds represented by structure B or the pharmaceutically acceptable salts thereof and the attendant limitations, wherein m is 1.

In certain embodiments, the present invention relates to any of the aforementioned compounds represented by structure B or the pharmaceutically acceptable salts thereof and the attendant limitations, wherein R represents independently for each occurrence H; and R' represents independently for each occurrence H.

In certain embodiments, the present invention relates to any of the aforementioned compounds represented by structure B or the pharmaceutically acceptable salts thereof and the attendant limitations, wherein R represents independently for each occurrence H; and R" represents H or alkyl.

In certain embodiments, the present invention relates to any of the aforementioned compounds represented by structure B or the pharmaceutically acceptable salts thereof and the attendant limitations, wherein R represents independently for each occurrence H; and R" represents H.

In certain embodiments, the present invention relates to any of the aforementioned compounds represented by structure B or the pharmaceutically acceptable salts thereof and the attendant limitations, wherein R' represents independently for each occurrence H; and R" represents H or alkyl.

In certain embodiments, the present invention relates to any of the aforementioned compounds represented by structure B or the pharmaceutically acceptable salts thereof and the attendant limitations, wherein R' represents independently for each occurrence H; and R" represents H.

In certain embodiments, the present invention relates to any of the aforementioned compounds represented by structure B or the pharmaceutically acceptable salts thereof and the attendant limitations, wherein R represents independently for each occurrence H; R' represents independently for each occurrence H; and m is 1.

In certain embodiments, the present invention relates to any of the aforementioned compounds represented by structure B or the pharmaceutically acceptable salts thereof and the attendant limitations, wherein R represents independently for each occurrence H; R" represents H or alkyl; and m is 1.

In certain embodiments, the present invention relates to any of the aforementioned compounds represented by structure B or the pharmaceutically acceptable salts thereof and the attendant limitations, wherein R represents independently for each occurrence H; R" represents H; and m is 1.

In certain embodiments, the present invention relates to any of the aforementioned compounds represented by structure B or the pharmaceutically acceptable salts thereof and the attendant limitations, wherein R' represents independently for each occurrence H; R" represents H or alkyl; and m is 1.

In certain embodiments, the present invention relates to any of the aforementioned compounds represented by structure B or the pharmaceutically acceptable salts thereof and the attendant limitations, wherein R' represents independently for each occurrence H; R" represents H; and m is 1.

In certain embodiments, the present invention relates to any of the aforementioned compounds represented by structure B or the pharmaceutically acceptable salts thereof and the attendant limitations, wherein R represents independently for each occurrence H; R' represents independently for each occurrence H; and R" represents H or alkyl.

In certain embodiments, the present invention relates to any of the aforementioned compounds represented by structure B or the pharmaceutically acceptable salts thereof and the attendant limitations, wherein R represents independently for each occurrence H; R' represents independently for each occurrence H; and R" represents H.

In certain embodiments, the present invention relates to any of the aforementioned compounds represented by structure B or the pharmaceutically acceptable salts thereof and the attendant limitations, wherein R represents independently for each occurrence H; R' represents independently for each occurrence H; R" represents H or alkyl; and m is 1.

In certain embodiments, the present invention relates to any of the aforementioned compounds represented by structure B or the pharmaceutically acceptable salts thereof and the attendant limitations, wherein R represents independently for each occurrence H; R' represents independently for each occurrence H; R" represents H; and m is 1.

In certain embodiments, the present invention relates to a compound represented by structure C, or a pharmaceutically acceptable salt thereof:

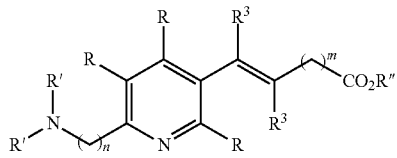

C wherein
R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl;

R' represents independently for each occurrence H, alkyl, alkenyl, alkynyl, aryl, heteroaryl, aralkyl, heteroaralkyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, formyl, acyl, amino, alkylamino, arylamino, heteroarylamino, aralkylamino, heteroaralkylamino, alkenylamino, alkynylamino, formylamino, acylamino, alkyloxycarbonyl, aryloxycarbonyl, heteroaryloxycarbonyl, aralkyloxycarbonyl, heteroaralkyloxycarbonyl, alkylaminocarbonyl, arylaminocarbonyl, heteroarylaminocarbonyl, aralkylaminocarbonyl, or heteroaralkylaminocarbonyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—;

R" represents independently for each occurrence H, alkyl, alkenyl, alkynyl, aryl, heteroaryl, aralkyl, or heteroaralkyl;

R$^3$ represents independently for each occurrence H, alkyl, alkenyl, alkynyl, aryl, heteroaryl, aralkyl, or heteroaralkyl;

n is 1, 2, 3, or 4; and
m is 1, 2, or 3.

In certain embodiments, the present invention relates to any of the aforementioned compounds represented by structure C or the pharmaceutically acceptable salts thereof and the attendant limitations, wherein R represents independently for each occurrence H, alkyl, fluoride, chloride, bromide, nitro, cyano, sulfonic acid, hydroxyl, alkoxyl, thiol, alkylthio, formyl, acyl, formyloxy, acyloxy, formylthio, acylthio, amino, alkylamino, formylamino, acylamino, or carboxylate.

In certain embodiments, the present invention relates to any of the aforementioned compounds represented by structure C or the pharmaceutically acceptable salts thereof and the attendant limitations, wherein R represents independently for each occurrence H, or alkyl.

In certain embodiments, the present invention relates to any of the aforementioned compounds represented by structure C or the pharmaceutically acceptable salts thereof and the attendant limitations, wherein R represents independently for each occurrence H.

In certain embodiments, the present invention relates to any of the aforementioned compounds represented by structure C or the pharmaceutically acceptable salts thereof and the attendant limitations, wherein R' represents independently for each occurrence H, alkyl, alkenyl, alkynyl, aryl, heteroaryl, aralkyl, or heteroaralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure C or the pharmaceutically acceptable salts thereof and the attendant limitations, wherein R' represents independently for each occurrence H, alkyl, or aralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure C or the pharmaceutically acceptable salts thereof and the attendant limitations, wherein the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure C or the pharmaceutically acceptable salts thereof and the attendant limitations, wherein the two instances of R' taken together represent —(CH$_2$)$_4$—.

In certain embodiments, the present invention relates to any of the aforementioned compounds represented by structure C or the pharmaceutically acceptable salts thereof and the attendant limitations, wherein R" represents H or alkyl.

In certain embodiments, the present invention relates to any of the aforementioned compounds represented by structure C or the pharmaceutically acceptable salts thereof and the attendant limitations, wherein R" represents H.

In certain embodiments, the present invention relates to any of the aforementioned compounds represented by structure C or the pharmaceutically acceptable salts thereof and the attendant limitations, wherein $R^3$ represents independently for each occurrence H or alkyl.

In certain embodiments, the present invention relates to any of the aforementioned compounds represented by structure C or the pharmaceutically acceptable salts thereof and the attendant limitations, wherein $R^3$ represents independently for each occurrence H.

In certain embodiments, the present invention relates to any of the aforementioned compounds represented by structure C or the pharmaceutically acceptable salts thereof and the attendant limitations, wherein n is 2.

In certain embodiments, the present invention relates to any of the aforementioned compounds represented by structure C or the pharmaceutically acceptable salts thereof and the attendant limitations, wherein m is 1.

In certain embodiments, the present invention relates to any of the aforementioned compounds represented by structure C or the pharmaceutically acceptable salts thereof and the attendant limitations, wherein R represents independently for each occurrence H; and $R^3$ represents independently for each occurrence H.

In certain embodiments, the present invention relates to any of the aforementioned compounds represented by structure C or the pharmaceutically acceptable salts thereof and the attendant limitations, wherein R represents independently for each occurrence H; R" represents H or alkyl; and $R^3$ represents independently for each occurrence H or alkyl.

In certain embodiments, the present invention relates to any of the aforementioned compounds represented by structure C or the pharmaceutically acceptable salts thereof and the attendant limitations, wherein R represents independently for each occurrence H; R" represents H; and $R^3$ represents independently for each occurrence H.

In certain embodiments, the present invention relates to any of the aforementioned compounds represented by structure C or the pharmaceutically acceptable salts thereof and the attendant limitations, wherein R represents independently for each occurrence H; the two instances of R' taken together represent —(CH$_2$)$_4$—; R" represents H or alkyl; and $R^3$ represents independently for each occurrence H or alkyl.

In certain embodiments, the present invention relates to any of the aforementioned compounds represented by structure C or the pharmaceutically acceptable salts thereof and the attendant limitations, wherein R represents independently for each occurrence H; the two instances of R' taken together represent —(CH$_2$)$_4$—; R" represents H; and $R^3$ represents independently for each occurrence H.

In certain embodiments, the present invention relates to any of the aforementioned compounds represented by structure C or the pharmaceutically acceptable salts thereof and the attendant limitations, wherein R represents independently for each occurrence H; the two instances of R' taken together represent —(CH$_2$)$_4$—; R" represents H or alkyl; $R^3$ represents independently for each occurrence H or alkyl; and n is 2.

In certain embodiments, the present invention relates to any of the aforementioned compounds represented by structure C or the pharmaceutically acceptable salts thereof and the attendant limitations, wherein R represents independently for each occurrence H; the two instances of R' taken together represent —(CH$_2$)$_4$—; R" represents H; $R^3$ represents independently for each occurrence H; and n is 2.

In certain embodiments, the present invention relates to any of the aforementioned compounds represented by structure C or the pharmaceutically acceptable salts thereof and the attendant limitations, wherein R represents independently for each occurrence H; $R^3$ represents independently for each occurrence H; and m is 1.

In certain embodiments, the present invention relates to any of the aforementioned compounds represented by structure C or the pharmaceutically acceptable salts thereof and the attendant limitations, wherein R represents independently for each occurrence H; R" represents H or alkyl; $R^3$ represents independently for each occurrence H or alkyl; and m is 1.

In certain embodiments, the present invention relates to any of the aforementioned compounds represented by structure C or the pharmaceutically acceptable salts thereof and the attendant limitations, wherein R represents independently for each occurrence H; R" represents H; $R^3$ represents independently for each occurrence H; and m is 1.

In certain embodiments, the present invention relates to any of the aforementioned compounds represented by structure C or the pharmaceutically acceptable salts thereof and the attendant limitations, wherein R represents independently for each occurrence H; the two instances of R' taken together represent —(CH$_2$)$_4$—; R" represents H or alkyl; $R^3$ represents independently for each occurrence H or alkyl; and m is 1.

In certain embodiments, the present invention relates to any of the aforementioned compounds represented by structure C or the pharmaceutically acceptable salts thereof and the attendant limitations, wherein R represents independently for each occurrence H; the two instances of R' taken together represent —(CH$_2$)$_4$—; R" represents H; $R^3$ represents independently for each occurrence H; and m is 1.

In certain embodiments, the present invention relates to any of the aforementioned compounds represented by structure C or the pharmaceutically acceptable salts thereof and the attendant limitations, wherein R represents independently for each occurrence H; the two instances of R' taken together represent —(CH$_2$)$_4$—; R" represents H or alkyl; $R^3$ represents independently for each occurrence H or alkyl; n is 2; and m is 1.

In certain embodiments, the present invention relates to any of the aforementioned compounds represented by structure C or the pharmaceutically acceptable salts thereof and the attendant limitations, wherein R represents independently for each occurrence H; the two instances of R' taken together represent —(CH$_2$)$_4$—; R" represents H; $R^3$ represents independently for each occurrence H; n is 2; and m is 1.

In certain embodiments, the present invention relates to a compound represented by structure D, or a pharmaceutically acceptable salt thereof:

wherein

X represents —CH$_2$—, —CH$_2$CH$_2$—, —CH$_2$CH$_2$CH$_2$—, —CH$_2$CH$_2$CH$_2$CH$_2$—, —CH═CH—, —CH═CHCH$_2$—, —CH$_2$CH═CH—, —CH═CHCH$_2$CH$_2$—, —CH$_2$CH═CHCH$_2$—, —CH$_2$CH$_2$CH═CH—, or —CH═CHCH═CH—;

Y represents —CO$_2$R", —SO$_3$H, —SO$_2$NH$_2$; —B(OH)$_2$, —PO$_3$H$_2$, or 5-tetrazolyl;

R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl;

R' represents independently for each occurrence H, alkyl, alkenyl, alkynyl, aryl, heteroaryl, aralkyl, heteroaralkyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, formyl, acyl, amino, alkylamino, arylamino, heteroarylamino, aralkylamino, heteroaralkylamino, alkenylamino, alkynylamino, formylamino, acylamino, alkyloxycarbonyl, aryloxycarbonyl, heteroaryloxycarbonyl, aralkyloxycarbonyl, heteroaralkyloxycarbonyl, alkylaminocarbonyl, arylaminocarbonyl, heteroarylaminocarbonyl, aralkylaminocarbonyl, or heteroaralkylaminocarbonyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—;

R'' represents independently for each occurrence H, alkyl, alkenyl, alkynyl, aryl, heteroaryl, aralkyl, or heteroaralkyl; and n is 1, 2, 3, or 4.

In certain embodiments, the present invention relates to any of the aforementioned compounds represented by structure D or the pharmaceutically acceptable salts thereof and the attendant limitations, wherein Y represents —CO$_2$R''.

In certain embodiments, the present invention relates to any of the aforementioned compounds represented by structure D or the pharmaceutically acceptable salts thereof and the attendant limitations, wherein Y represents —CO$_2$R''; and R'' represents H.

In certain embodiments, the present invention relates to any of the aforementioned compounds represented by structure D or the pharmaceutically acceptable salts thereof and the attendant limitations, wherein R represents independently for each occurrence H, alkyl, fluoride, chloride, bromide, nitro, cyano, sulfonic acid, hydroxyl, alkoxyl, thiol, alkylthio, formyl, acyl, formyloxy, acyloxy, formylthio, acylthio, amino, alkylamino, formylamino, acylamino, or carboxylate.

In certain embodiments, the present invention relates to any of the aforementioned compounds represented by structure D or the pharmaceutically acceptable salts thereof and the attendant limitations, wherein R represents independently for each occurrence H, or alkyl.

In certain embodiments, the present invention relates to any of the aforementioned compounds represented by structure D or the pharmaceutically acceptable salts thereof and the attendant limitations, wherein R represents independently for each occurrence H.

In certain embodiments, the present invention relates to any of the aforementioned compounds represented by structure D or the pharmaceutically acceptable salts thereof and the attendant limitations, wherein R' represents independently for each occurrence H, alkyl, alkenyl, alkynyl, aryl, heteroaryl, aralkyl, or heteroaralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure D or the pharmaceutically acceptable salts thereof and the attendant limitations, wherein R' represents independently for each occurrence H, alkyl, or aralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure D or the pharmaceutically acceptable salts thereof and the attendant limitations, wherein the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure D or the pharmaceutically acceptable salts thereof and the attendant limitations, wherein the two instances of R' taken together represent —(CH$_2$)$_4$—.

In certain embodiments, the present invention relates to any of the aforementioned compounds represented by structure D or the pharmaceutically acceptable salts thereof and the attendant limitations, wherein R'' represents H or alkyl.

In certain embodiments, the present invention relates to any of the aforementioned compounds represented by structure D or the pharmaceutically acceptable salts thereof and the attendant limitations, wherein R'' represents H.

In certain embodiments, the present invention relates to any of the aforementioned compounds represented by structure D or the pharmaceutically acceptable salts thereof and the attendant limitations, wherein n is 2.

In certain embodiments, the present invention relates to any of the aforementioned compounds represented by structure D or the pharmaceutically acceptable salts thereof and the attendant limitations, wherein R represents independently for each occurrence H; and n is 2.

In certain embodiments, the present invention relates to any of the aforementioned compounds represented by structure D or the pharmaceutically acceptable salts thereof and the attendant limitations, wherein R represents independently for each occurrence H; and the two instances of R' taken together represent —(CH$_2$)$_4$—.

In certain embodiments, the present invention relates to any of the aforementioned compounds represented by structure D or the pharmaceutically acceptable salts thereof and the attendant limitations, wherein R represents independently for each occurrence H; the two instances of R' taken together represent —(CH$_2$)$_4$—; and n is 2.

In certain embodiments, the present invention relates to any of the aforementioned compounds represented by structure D or the pharmaceutically acceptable salts thereof and the attendant limitations, wherein R represents independently for each occurrence H; and R'' represents H or alkyl.

In certain embodiments, the present invention relates to any of the aforementioned compounds represented by structure D or the pharmaceutically acceptable salts thereof and the attendant limitations, wherein R represents independently for each occurrence H; R'' represents H or alkyl; and n is 2.

In certain embodiments, the present invention relates to any of the aforementioned compounds represented by structure D or the pharmaceutically acceptable salts thereof and the attendant limitations, wherein R represents independently for each occurrence H, or alkyl; R' represents independently for each occurrence H, alkyl, alkenyl, alkynyl, aryl, heteroaryl, aralkyl, or heteroaralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—; and R" represents H or alkyl.

In certain embodiments, the present invention relates to any of the aforementioned compounds represented by structure D or the pharmaceutically acceptable salts thereof and the attendant limitations, wherein R represents independently for each occurrence H, or alkyl; the two instances of R' taken together represent —(CH$_2$)$_4$—; and R" represents H or alkyl.

In certain embodiments, the present invention relates to any of the aforementioned compounds represented by structure D or the pharmaceutically acceptable salts thereof and the attendant limitations, wherein R represents independently for each occurrence H; the two instances of R' taken together represent —(CH$_2$)$_4$—; and R" represents H or alkyl.

In certain embodiments, the present invention relates to any of the aforementioned compounds represented by structure D or the pharmaceutically acceptable salts thereof and the attendant limitations, wherein R represents independently for each occurrence H; the two instances of R' taken together represent —(CH$_2$)$_4$—; R" represents H or alkyl; and n is 2.

In certain embodiments, the present invention relates to any of the aforementioned compounds represented by structure D or the pharmaceutically acceptable salts thereof and the attendant limitations, wherein R represents independently for each occurrence H; the two instances of R' taken together represent —(CH$_2$)$_4$—; R" represents H; and n is 2.

In certain embodiments, the present invention relates to any of the aforementioned compounds represented by structure D or the pharmaceutically acceptable salts thereof and the attendant limitations, wherein Y represents —CO$_2$R"; R" represents H; R represents independently for each occurrence H; and n is 2.

In certain embodiments, the present invention relates to any of the aforementioned compounds represented by structure D or the pharmaceutically acceptable salts thereof and the attendant limitations, wherein Y represents —CO$_2$R"; R" represents H; R represents independently for each occurrence H; and the two instances of R' taken together represent —(CH$_2$)$_4$—.

In certain embodiments, the present invention relates to any of the aforementioned compounds represented by structure D or the pharmaceutically acceptable salts thereof and the attendant limitations, wherein Y represents —CO$_2$R"; R" represents H; R represents independently for each occurrence H; the two instances of R' taken together represent —(CH$_2$)$_4$—; and n is 2.

In certain embodiments, the present invention relates to any of the aforementioned compounds represented by structure D or the pharmaceutically acceptable salts thereof and the attendant limitations, wherein Y represents —CO$_2$R"; R represents independently for each occurrence H; and R" represents H or alkyl.

In certain embodiments, the present invention relates to any of the aforementioned compounds represented by structure D or the pharmaceutically acceptable salts thereof and the attendant limitations, wherein Y represents —CO$_2$R"; R represents independently for each occurrence H; R" represents H or alkyl; and n is 2.

In certain embodiments, the present invention relates to any of the aforementioned compounds represented by structure D or the pharmaceutically acceptable salts thereof and the attendant limitations, wherein Y represents —CO$_2$R"; R represents independently for each occurrence H, or alkyl; R' represents independently for each occurrence H, alkyl, alkenyl, alkynyl, aryl, heteroaryl, aralkyl, or heteroaralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—; and R" represents H or alkyl.

In certain embodiments, the present invention relates to any of the aforementioned compounds represented by structure D or the pharmaceutically acceptable salts thereof and the attendant limitations, wherein Y represents —CO$_2$R"; R represents independently for each occurrence H, or alkyl; the two instances of R' taken together represent —(CH$_2$)$_4$—; and R" represents H or alkyl.

In certain embodiments, the present invention relates to any of the aforementioned compounds represented by structure D or the pharmaceutically acceptable salts thereof and the attendant limitations, wherein Y represents —CO$_2$R"; R represents independently for each occurrence H; the two instances of R' taken together represent —(CH$_2$)$_4$—; and R" represents H or alkyl.

In certain embodiments, the present invention relates to any of the aforementioned compounds represented by structure D or the pharmaceutically acceptable salts thereof and the attendant limitations, wherein Y represents —CO$_2$R"; R represents independently for each occurrence H; the two instances of R' taken together represent —(CH$_2$)$_4$—; R" represents H or alkyl; and n is 2.

In certain embodiments, the present invention relates to any of the aforementioned compounds represented by structure D or the pharmaceutically acceptable salts thereof and the attendant limitations, wherein Y represents —CO$_2$R"; R represents independently for each occurrence H; the two instances of R' taken together represent —(CH$_2$)$_4$—; R" represents H; and n is 2.

In certain embodiments, the present invention relates to a compound represented by structure E, or a pharmaceutically acceptable salt thereof:

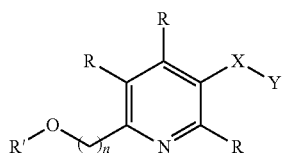

E wherein
X represents —CH$_2$—, —CH$_2$CH$_2$—, —CH$_2$CH$_2$CH$_2$—, —CH$_2$CH$_2$CH$_2$CH$_2$—, —CH═CH—, —CH═CHCH$_2$—, —CH$_2$CH═CH—, —CH═CHCH$_2$CH$_2$—, —CH$_2$CH═CHCH$_2$—, —CH$_2$CH$_2$CH═CH—, or —CH═CHCH═CH—;

Y represents —CO$_2$R", —SO$_3$H, —SO$_2$NH$_2$; —B(OH)$_2$, —PO$_3$H$_2$, or 5-tetrazolyl;

R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl;

R' represents independently for each occurrence H, alkyl, alkenyl, alkynyl, aryl, heteroaryl, aralkyl, heteroaralkyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, formyl, acyl, amino, alkylamino, arylamino, heteroarylamino, aralkylamino, heteroaralkylamino, alkenylamino, alkynylamino, formylamino, acylamino, alkyloxycarbonyl, aryloxycarbonyl, heteroaryloxycarbonyl, aralkyloxycarbonyl, heteroaralkyloxycarbonyl, alkylaminocarbonyl, arylaminocarbonyl, heteroarylaminocarbonyl, aralkylaminocarbonyl, or heteroaralkylaminocarbonyl;

R" represents independently for each occurrence H, alkyl, alkenyl, alkynyl, aryl, heteroaryl, aralkyl, or heteroaralkyl; and n is 1, 2, 3, or 4.

In certain embodiments, the present invention relates to any of the aforementioned compounds represented by structure E or the pharmaceutically acceptable salts thereof and the attendant limitations, wherein Y represents —CO$_2$R".

In certain embodiments, the present invention relates to any of the aforementioned compounds represented by structure E or the pharmaceutically acceptable salts thereof and the attendant limitations, wherein Y represents —CO$_2$R"; and R" represents H.

In certain embodiments, the present invention relates to any of the aforementioned compounds represented by structure E or the pharmaceutically acceptable salts thereof and the attendant limitations, wherein R represents independently for each occurrence H, alkyl, fluoride, chloride, bromide, nitro, cyano, sulfonic acid, hydroxyl, alkoxyl, thiol, alkylthio, formyl, acyl, formyloxy, acyloxy, formylthio, acylthio, amino, alkylamino, formylamino, acylamino, or carboxylate.

In certain embodiments, the present invention relates to any of the aforementioned compounds represented by structure E or the pharmaceutically acceptable salts thereof and the attendant limitations, wherein R represents independently for each occurrence H, or alkyl.

In certain embodiments, the present invention relates to any of the aforementioned compounds represented by structure E or the pharmaceutically acceptable salts thereof and the attendant limitations, wherein R represents independently for each occurrence H.

In certain embodiments, the present invention relates to any of the aforementioned compounds represented by structure E or the pharmaceutically acceptable salts thereof and the attendant limitations, wherein R' represents independently for each occurrence H, alkyl, alkenyl, alkynyl, aryl, heteroaryl, aralkyl, or heteroaralkyl.

In certain embodiments, the present invention relates to any of the aforementioned compounds represented by structure E or the pharmaceutically acceptable salts thereof and the attendant limitations, wherein R' represents independently for each occurrence H, alkyl, or aralkyl.

In certain embodiments, the present invention relates to any of the aforementioned compounds represented by structure E or the pharmaceutically acceptable salts thereof and the attendant limitations, wherein R" represents H or alkyl.

In certain embodiments, the present invention relates to any of the aforementioned compounds represented by structure E or the pharmaceutically acceptable salts thereof and the attendant limitations, wherein R" represents H.

In certain embodiments, the present invention relates to any of the aforementioned compounds represented by structure E or the pharmaceutically acceptable salts thereof and the attendant limitations, wherein n is 2.

In certain embodiments, the present invention relates to any of the aforementioned compounds represented by structure E or the pharmaceutically acceptable salts thereof and the attendant limitations, wherein R represents independently for each occurrence H; and n is 2.

In certain embodiments, the present invention relates to any of the aforementioned compounds represented by structure E or the pharmaceutically acceptable salts thereof and the attendant limitations, wherein R represents independently for each occurrence H; and R" represents H or alkyl.

In certain embodiments, the present invention relates to any of the aforementioned compounds represented by structure E or the pharmaceutically acceptable salts thereof and the attendant limitations, wherein R represents independently for each occurrence H; R" represents H or alkyl; and n is 2.

In certain embodiments, the present invention relates to any of the aforementioned compounds represented by structure E or the pharmaceutically acceptable salts thereof and the attendant limitations, wherein R represents independently for each occurrence H, or alkyl; R' represents independently for each occurrence H, alkyl, alkenyl, alkynyl, aryl, heteroaryl, aralkyl, or heteroaralkyl; and R" represents H or alkyl.

In certain embodiments, the present invention relates to any of the aforementioned compounds represented by structure E or the pharmaceutically acceptable salts thereof and the attendant limitations, wherein Y represents —CO$_2$R"; R" represents H; R represents independently for each occurrence H; and n is 2.

In certain embodiments, the present invention relates to any of the aforementioned compounds represented by structure E or the pharmaceutically acceptable salts thereof and the attendant limitations, wherein Y represents —CO$_2$R"; R represents independently for each occurrence H; and R" represents H or alkyl.

In certain embodiments, the present invention relates to any of the aforementioned compounds represented by structure E or the pharmaceutically acceptable salts thereof and the attendant limitations, wherein Y represents —CO$_2$R"; R represents independently for each occurrence H; R" represents H or alkyl; and n is 2.

In certain embodiments, the present invention relates to any of the aforementioned compounds represented by structure E or the pharmaceutically acceptable salts thereof and the attendant limitations, wherein Y represents —CO$_2$R"; R represents independently for each occurrence H, or alkyl; R' represents independently for each occurrence H, alkyl, alkenyl, alkynyl, aryl, heteroaryl, aralkyl, or heteroaralkyl; and R" represents H or alkyl.

In certain embodiments, the present invention relates to a compound represented by structure F, or a pharmaceutically acceptable salt thereof:

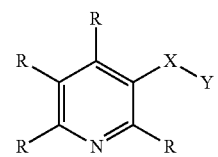

wherein
X represents —CH$_2$—, —CH$_2$CH$_2$—, —CH$_2$CH$_2$CH$_2$—, —CH$_2$CH$_2$CH$_2$CH$_2$—, —CH═CH—, —CH═CHCH$_2$—, —CH₂CH=CH—, —CH=CHCH₂CH₂—, —CH₂CH=CHCH₂—, —CH₂CH₂CH=CH—, or —CH=CHCH=CH—;

Y represents —CO₂R″, —SO₃H, —SO₂NH₂; —B(OH)₂, —PO₃H₂, or 5-tetrazolyl;

R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl; and R″ represents independently for each occurrence H, alkyl, alkenyl, alkynyl, aryl, heteroaryl, aralkyl, or heteroaralkyl.

In certain embodiments, the present invention relates to any of the aforementioned compounds represented by structure F or the pharmaceutically acceptable salts thereof and the attendant limitations, wherein Y represents —CO₂R″.

In certain embodiments, the present invention relates to any of the aforementioned compounds represented by structure F or the pharmaceutically acceptable salts thereof and the attendant limitations, wherein Y represents —CO₂R″; and R″ represents H.

In certain embodiments, the present invention relates to any of the aforementioned compounds represented by structure F or the pharmaceutically acceptable salts thereof and the attendant limitations, wherein R represents independently for each occurrence H, alkyl, fluoride, chloride, bromide, nitro, cyano, sulfonic acid, hydroxyl, alkoxyl, thiol, alkylthio, formyl, acyl, formyloxy, acyloxy, formylthio, acylthio, amino, alkylamino, formylamino, acylamino, or carboxylate.

In certain embodiments, the present invention relates to any of the aforementioned compounds represented by structure F or the pharmaceutically acceptable salts thereof and the attendant limitations, wherein R represents independently for each occurrence H, or alkyl.

In certain embodiments, the present invention relates to any of the aforementioned compounds represented by structure F or the pharmaceutically acceptable salts thereof and the attendant limitations, wherein R represents independently for each occurrence H.

In certain embodiments, the present invention relates to any of the aforementioned compounds represented by structure F or the pharmaceutically acceptable salts thereof and the attendant limitations, wherein R″ represents H or alkyl.

In certain embodiments, the present invention relates to any of the aforementioned compounds represented by structure F or the pharmaceutically acceptable salts thereof and the attendant limitations, wherein R″ represents H.

In certain embodiments, the present invention relates to any of the aforementioned compounds represented by structure F or the pharmaceutically acceptable salts thereof and the attendant limitations, wherein R represents independently for each occurrence H; and R″ represents H or alkyl.

In certain embodiments, the present invention relates to any of the aforementioned compounds represented by structure F or the pharmaceutically acceptable salts thereof and the attendant limitations, wherein R represents independently for each occurrence H; and R″ represents H.

In certain embodiments, the present invention relates to any of the aforementioned compounds represented by structure F or the pharmaceutically acceptable salts thereof and the attendant limitations, wherein Y represents —CO₂R″; R″ represents H; R represents independently for each occurrence H, alkyl, fluoride, chloride, bromide, nitro, cyano, sulfonic acid, hydroxyl, alkoxyl, thiol, alkylthio, formyl, acyl, formyloxy, acyloxy, formylthio, acylthio, amino, alkylamino, formylamino, acylamino, or carboxylate.

In certain embodiments, the present invention relates to any of the aforementioned compounds represented by structure F or the pharmaceutically acceptable salts thereof and the attendant limitations, wherein Y represents —CO₂R″; R″ represents H; R represents independently for each occurrence H, or alkyl.

In certain embodiments, the present invention relates to any of the aforementioned compounds represented by structure F or the pharmaceutically acceptable salts thereof and the attendant limitations, wherein Y represents —CO₂R″; R″ represents H; R represents independently for each occurrence H.

In certain embodiments, the present invention relates to any of the aforementioned compounds represented by structure F or the pharmaceutically acceptable salts thereof and the attendant limitations, wherein Y represents —CO₂R″; and R″ represents H or alkyl.

In certain embodiments, the present invention relates to a compound represented by structure G, or a pharmaceutically acceptable salt thereof:

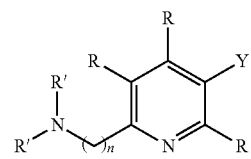

wherein

Y represents —SO₃H, —SO₂NH₂; —B(OH)₂, —PO₃H₂, or 5-tetrazolyl;

R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl;

R' represents independently for each occurrence H, alkyl, alkenyl, alkynyl, aryl, heteroaryl, aralkyl, heteroaralkyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, formyl, acyl, amino, alkylamino, arylamino, heteroarylamino, aralkylamino, heteroaralkylamino, alkenylamino, alkynylamino, formylamino, acylamino, alkyloxycarbonyl, aryloxycarbonyl, heteroaryloxycarbonyl, aralkyloxycarbonyl, heteroaralkyloxycarbonyl, alkylaminocarbonyl, arylaminocarbonyl, heteroarylaminocarbonyl, aralkylaminocarbonyl, or heteroaralkylaminocarbonyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—; and n is 1, 2, 3, or 4.

In certain embodiments, the present invention relates to any of the aforementioned compounds represented by structure G or the pharmaceutically acceptable salts thereof and the attendant limitations, wherein R represents independently for each occurrence H, alkyl, fluoride, chloride, bromide, nitro, cyano, sulfonic acid, hydroxyl, alkoxyl, thiol, alkylthio, formyl, acyl, formyloxy, acyloxy, formylthio, acylthio, amino, alkylamino, formylamino, acylamino, or carboxylate.

In certain embodiments, the present invention relates to any of the aforementioned compounds represented by structure G or the pharmaceutically acceptable salts thereof and the attendant limitations, wherein R represents independently for each occurrence H, or alkyl.

In certain embodiments, the present invention relates to any of the aforementioned compounds represented by structure G or the pharmaceutically acceptable salts thereof and the attendant limitations, wherein R represents independently for each occurrence H.

In certain embodiments, the present invention relates to any of the aforementioned compounds represented by structure G or the pharmaceutically acceptable salts thereof and the attendant limitations, wherein R' represents independently for each occurrence H, alkyl, alkenyl, alkynyl, aryl, heteroaryl, aralkyl, or heteroaralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure G or the pharmaceutically acceptable salts thereof and the attendant limitations, wherein R' represents independently for each occurrence H, alkyl, or aralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure G or the pharmaceutically acceptable salts thereof and the attendant limitations, wherein the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure G or the pharmaceutically acceptable salts thereof and the attendant limitations, wherein the two instances of R' taken together represent —(CH$_2$)$_4$—.

In certain embodiments, the present invention relates to any of the aforementioned compounds represented by structure G or the pharmaceutically acceptable salts thereof and the attendant limitations, wherein n is 2.

In certain embodiments, the present invention relates to any of the aforementioned compounds represented by structure G or the pharmaceutically acceptable salts thereof and the attendant limitations, wherein R represents independently for each occurrence H; and n is 2.

In certain embodiments, the present invention relates to any of the aforementioned compounds represented by structure G or the pharmaceutically acceptable salts thereof and the attendant limitations, wherein R represents independently for each occurrence H; and the two instances of R' taken together represent —(CH$_2$)$_4$—.

In certain embodiments, the present invention relates to any of the aforementioned compounds represented by structure G or the pharmaceutically acceptable salts thereof and the attendant limitations, wherein R represents independently for each occurrence H; the two instances of R' taken together represent —(CH$_2$)$_4$—; and n is 2.

In certain embodiments, the present invention relates to a compound represented by structure H, or a pharmaceutically acceptable salt thereof:

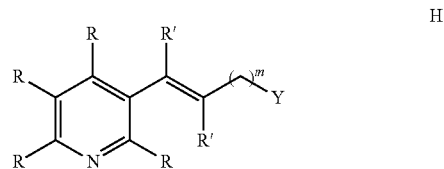

wherein

Y represents —SO$_3$H, —SO$_2$NH$_2$; —B(OH)$_2$, —PO$_3$H$_2$, or 5-tetrazolyl;

R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl;

R' represents independently for each occurrence H, alkyl, alkenyl, alkynyl, aryl, heteroaryl, aralkyl, or heteroaralkyl; and m is 1, 2, or 3.

In certain embodiments, the present invention relates to any of the aforementioned compounds represented by structure H or the pharmaceutically acceptable salts thereof and the attendant limitations, wherein R represents independently for each occurrence H, alkyl, fluoride, chloride, bromide, nitro, cyano, sulfonic acid, hydroxyl, alkoxyl, thiol, alkylthio, formyl, acyl, formyloxy, acyloxy, formylthio, acylthio, amino, alkylamino, formylamino, acylamino, or carboxylate.

In certain embodiments, the present invention relates to any of the aforementioned compounds represented by structure H or the pharmaceutically acceptable salts thereof and the attendant limitations, wherein R represents independently for each occurrence H, or alkyl.

In certain embodiments, the present invention relates to any of the aforementioned compounds represented by structure H or the pharmaceutically acceptable salts thereof and the attendant limitations, wherein R represents independently for each occurrence H.

In certain embodiments, the present invention relates to any of the aforementioned compounds represented by structure H or the pharmaceutically acceptable salts thereof and the attendant limitations, wherein R' represents independently for each occurrence H or alkyl.

In certain embodiments, the present invention relates to any of the aforementioned compounds represented by structure H or the pharmaceutically acceptable salts thereof and the attendant limitations, wherein R' represents independently for each occurrence H.

In certain embodiments, the present invention relates to any of the aforementioned compounds represented by structure H or the pharmaceutically acceptable salts thereof and the attendant limitations, wherein m is 1.

In certain embodiments, the present invention relates to any of the aforementioned compounds represented by structure H or the pharmaceutically acceptable salts thereof and the attendant limitations, wherein R represents independently for each occurrence H; and R' represents independently for each occurrence H.

In certain embodiments, the present invention relates to any of the aforementioned compounds represented by structure H or the pharmaceutically acceptable salts thereof and the attendant limitations, wherein R represents independently for each occurrence H; R' represents independently for each occurrence H; and m is 1.

In certain embodiments, the present invention relates to a compound represented by structure I, or a pharmaceutically acceptable salt thereof:

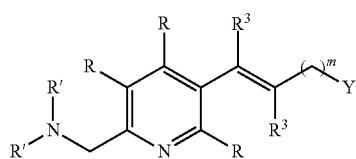

I wherein

Y represents —SO$_3$H, —SO$_2$NH$_2$; —B(OH)$_2$, —PO$_3$H$_2$, or 5-tetrazolyl;

R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl;

R' represents independently for each occurrence H, alkyl, alkenyl, alkynyl, aryl, heteroaryl, aralkyl, heteroaralkyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, formyl, acyl, amino, alkylamino, arylamino, heteroarylamino, aralkylamino, heteroaralkylamino, alkenylamino, alkynylamino, formylamino, acylamino, alkyloxycarbonyl, aryloxycarbonyl, heteroaryloxycarbonyl, aralkyloxycarbonyl, heteroaralkyloxycarbonyl, alkylaminocarbonyl, arylaminocarbonyl, heteroarylaminocarbonyl, aralkylaminocarbonyl, or heteroaralkylaminocarbonyl; or the two instances of R' taken together represent —(CH$_2$)$_2$—; —(CH$_2$)$_3$—, —(CH$_2$)$_4$—, —(CH$_2$)$_5$—, or —(CH$_2$)$_6$;

R$^3$ represents independently for each occurrence H, alkyl, alkenyl, alkynyl, aryl, heteroaryl, aralkyl, or heteroaralkyl;

n is 1, 2, 3, or 4; and m is 1, 2, or 3.

In certain embodiments, the present invention relates to any of the aforementioned compounds represented by structure I or the pharmaceutically acceptable salts thereof and the attendant limitations, wherein R represents independently for each occurrence H, alkyl, fluoride, chloride, bromide, nitro, cyano, sulfonic acid, hydroxyl, alkoxyl, thiol, alkylthio, formyl, acyl, formyloxy, acyloxy, formylthio, acylthio, amino, alkylamino, formylamino, acylamino, or carboxylate.

In certain embodiments, the present invention relates to any of the aforementioned compounds represented by structure I or the pharmaceutically acceptable salts thereof and the attendant limitations, wherein R represents independently for each occurrence H, or alkyl.

In certain embodiments, the present invention relates to any of the aforementioned compounds represented by structure I or the pharmaceutically acceptable salts thereof and the attendant limitations, wherein R represents independently for each occurrence H.

In certain embodiments, the present invention relates to any of the aforementioned compounds represented by structure I or the pharmaceutically acceptable salts thereof and the attendant limitations, wherein R' represents independently for each occurrence H, alkyl, alkenyl, alkynyl, aryl, heteroaryl, aralkyl, or heteroaralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure I or the pharmaceutically acceptable salts thereof and the attendant limitations, wherein R' represents independently for each occurrence H, alkyl, or aralkyl; or the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure I or the pharmaceutically acceptable salts thereof and the attendant limitations, wherein the two instances of R' taken together represent —(CH$_2$)$_2$—, —(CH$_2$)$_3$—, —(CH$_2$)$_4$—, —(CH$_2$)$_5$—, or —(CH$_2$)$_6$—.

In certain embodiments, the present invention relates to any of the aforementioned compounds represented by structure I or the pharmaceutically acceptable salts thereof and the attendant limitations, wherein the two instances of R' taken together represent —(CH$_2$)$_4$—.

In certain embodiments, the present invention relates to any of the aforementioned compounds represented by structure I or the pharmaceutically acceptable salts thereof and the attendant limitations, wherein $R^3$ represents independently for each occurrence H or alkyl.

In certain embodiments, the present invention relates to any of the aforementioned compounds represented by structure I or the pharmaceutically acceptable salts thereof and the attendant limitations, wherein $R^3$ represents independently for each occurrence H.

In certain embodiments, the present invention relates to any of the aforementioned compounds represented by structure I or the pharmaceutically acceptable salts thereof and the attendant limitations, wherein n is 2.

In certain embodiments, the present invention relates to any of the aforementioned compounds represented by structure I or the pharmaceutically acceptable salts thereof and the attendant limitations, wherein m is 1.

In certain embodiments, the present invention relates to any of the aforementioned compounds represented by structure I or the pharmaceutically acceptable salts thereof and the attendant limitations, wherein R represents independently for each occurrence H; and $R^3$ represents independently for each occurrence H.

In certain embodiments, the present invention relates to any of the aforementioned compounds represented by structure I or the pharmaceutically acceptable salts thereof and the attendant limitations, wherein R represents independently for each occurrence H; $R^3$ represents independently for each occurrence H; and m is 1.

In certain embodiments, the present invention relates to any of the aforementioned compounds represented by structure I or the pharmaceutically acceptable salts thereof and the attendant limitations, wherein R represents independently for each occurrence H; the two instances of R' taken together represent $—(CH_2)_4—$; $R^3$ represents independently for each occurrence H; and m is 1.

In certain embodiments, the present invention relates to any of the aforementioned compounds represented by structure I or the pharmaceutically acceptable salts thereof and the attendant limitations, wherein R represents independently for each occurrence H; the two instances of R' taken together represent $—(CH_2)_4—$; $R^3$ represents independently for each occurrence H or alkyl; n is 2; and m is 1.

In certain embodiments, the present invention relates to any of the aforementioned compounds represented by structure I or the pharmaceutically acceptable salts thereof and the attendant limitations, wherein R represents independently for each occurrence H; the two instances of R' taken together represent $—(CH_2)_4—$; $R^3$ represents independently for each occurrence H; n is 2; and m is 1.

In certain embodiments, the present invention relates to a pharmaceutical composition, comprising a compound of the present invention or a pharmaceutically acceptable salt thereof; and a pharmaceutically acceptable excipient.

In certain embodiments, the present invention relates to a pharmaceutical composition, comprising a compound of the present invention or a pharmaceutically acceptable salt thereof; niacin; and a pharmaceutically acceptable excipient.

In certain embodiments, the present invention relates to a pharmaceutical composition, comprising a compound of the present invention or a pharmaceutically acceptable salt thereof; a statin selected from the group consisting of atorvastatin, cerivastatin, fluvastatin, lovastatin, mevastatin, pitavastatin, pravastatin, rosuvastatin, simvastatin, gemcabene, and probucol; and a pharmaceutically acceptable excipient.

In certain embodiments, the present invention relates to a pharmaceutical composition, comprising a compound of the present invention or a pharmaceutically acceptable salt thereof; niacin; a statin selected from the group consisting of atorvastatin, cerivastatin, fluvastatin, lovastatin, mevastatin, pitavastatin, pravastatin, rosuvastatin, simvastatin, gemcabene, and probucol; and a pharmaceutically acceptable excipient.

In certain embodiments, the present invention relates to any of the aforementioned pharmaceutical compositions and the attendant limitations, wherein said statin is lovastatin or atorvastatin.

In certain embodiments, the present invention relates to a pharmaceutical composition, comprising a compound of the present invention or a pharmaceutically acceptable salt thereof; a glitazone selected from the group consisting of troglitazone, rosiglitazone, and pioglitazone; and a pharmaceutically acceptable excipient.

In certain embodiments, the present invention relates to a pharmaceutical composition, comprising a compound of the present invention or a pharmaceutically acceptable salt thereof; niacin; a glitazone selected from the group consisting of troglitazone, rosiglitazone, and pioglitazone; and a pharmaceutically acceptable excipient.

In certain embodiments, the present invention relates to a pharmaceutical composition, comprising a compound of the present invention or a pharmaceutically acceptable salt thereof; a fibrate selected from the group consisting of fenofibrate and bezafibrate; and a pharmaceutically acceptable excipient.

In certain embodiments, the present invention relates to a pharmaceutical composition, comprising a compound of the present invention or a pharmaceutically acceptable salt thereof; niacin; a fibrate selected from the group consisting of fenofibrate and bezafibrate; and a pharmaceutically acceptable excipient.

Methods of the Invention

A method of treating hyperlipidemia, hypercholesterolemia, atherosclerosis, coronary artery disease, congestive heart failure, cardiovascular disease, hypertension, coronary heart disease, angina, pellagra, Hartnup's syndrome, carcinoid syndrome, arterial occlusive disease, obesity, hypothyroidism, vasoconstriction, osteoarthritis, rheumatoid arthritis, diabetes, Alzheimer's disease, lipodystrophy, or dyslipidemia, comprising the step of:

administering to a mammal in need thereof a therapeutically effective amount of a compound of the present invention.

A method of treating hyperlipidemia, comprising the step of:

administering to a mammal in need thereof a therapeutically effective amount of a compound of the present invention.

A method of raising serum high-density lipoprotein (HDL) levels, comprising the step of:

administering to a mammal in need thereof a therapeutically effective amount of a compound of the present invention.

A method of lowering serum low-density lipoprotein (LDL) levels, comprising the step of:

administering to a mammal in need thereof a therapeutically effective amount of a compound of the present invention.

A method of lowering serum lipoprotein (a) (Lp(a)) levels, comprising the step of:

administering to a mammal in need thereof a therapeutically effective amount of a compound of the present invention.

A method of treating hyperlipidemia, hypercholesterolemia, atherosclerosis, coronary artery disease, congestive heart failure, cardiovascular disease, hypertension, coronary heart disease, angina, pellagra, Hartnup's syndrome, carcinoid syndrome, arterial occlusive disease, obesity, hypothyroidism, vasoconstriction, osteoarthritis, rheumatoid arthritis, diabetes, Alzheimer's disease, lipodystrophy, or dyslipidemia, comprising the step of:

co-administering to a mammal in need thereof a therapeutically effective amount of a compound of the present invention; and a therapeutically effective amount of niacin.

A method of treating hyperlipidemia, comprising the step of:

co-administering to a mammal in need thereof a therapeutically effective amount of a compound of the present invention; and a therapeutically effective amount of niacin.

A method of raising serum high-density lipoprotein (HDL) levels in a mammal, comprising the step of:

co-administering to a mammal in need thereof a therapeutically effective amount of a compound of the present invention; and a therapeutically effective amount of niacin.

A method of lowering serum low-density lipoprotein (LDL) levels in a mammal, comprising the step of:

co-administering to a mammal in need thereof a therapeutically effective amount of a compound of the present invention; and a therapeutically effective amount of niacin.

A method of lowering serum lipoprotein (a) (Lp(a)) levels in a mammal, comprising the step of:

co-administering to a mammal in need thereof a therapeutically effective amount of a compound of the present invention; and a therapeutically effective amount of niacin.

A method of treating hyperlipidemia, hypercholesterolemia, atherosclerosis, coronary artery disease, congestive heart failure, cardiovascular disease, hypertension, coronary heart disease, angina, pellagra, Hartnup's syndrome, carcinoid syndrome, arterial occlusive disease, obesity, hypothyroidism, vasoconstriction, osteoarthritis, rheumatoid arthritis, diabetes, Alzheimer's disease, lipodystrophy, or dyslipidemia, comprising the step of:

co-administering to a mammal in need thereof a therapeutically effective amount of a compound of the present invention; and a therapeutically effective amount of a statin selected from the group consisting of atorvastatin, cerivastatin, fluvastatin, lovastatin, mevastatin, pitavastatin, pravastatin, rosuvastatin, simvastatin, gemcabene, and probucol.

A method of treating hyperlipidemia, comprising the step of:

co-administering to a mammal in need thereof a therapeutically effective amount of a compound of the present invention; and a therapeutically effective amount of a statin selected from the group consisting of atorvastatin, cerivastatin, fluvastatin, lovastatin, mevastatin, pitavastatin, pravastatin, rosuvastatin, simvastatin, gemcabene, and probucol.

A method of raising serum high-density lipoprotein (HDL) levels in a mammal, comprising the step of:

co-administering to a mammal in need thereof a therapeutically effective amount of a compound of the present invention; and a therapeutically effective amount of a statin selected from the group consisting of atorvastatin, cerivastatin, fluvastatin, lovastatin, mevastatin, pitavastatin, pravastatin, rosuvastatin, simvastatin, gemcabene, and probucol.

A method of lowering serum low-density lipoprotein (LDL) levels in a mammal, comprising the step of:

co-administering to a mammal in need thereof a therapeutically effective amount of a compound of the present invention; and a therapeutically effective amount of a statin selected from the group consisting of atorvastatin, cerivastatin, fluvastatin, lovastatin, mevastatin, pitavastatin, pravastatin, rosuvastatin, simvastatin, gemcabene, and probucol.

A method of lowering serum lipoprotein (a) (Lp(a)) levels in a mammal, comprising the step of:

co-administering to a mammal in need thereof a therapeutically effective amount of a compound of the present invention; and a therapeutically effective amount of a statin selected from the group consisting of atorvastatin, cerivastatin, fluvastatin, lovastatin, mevastatin, pitavastatin, pravastatin, rosuvastatin, simvastatin, gemcabene, and probucol.

A method of treating hyperlipidemia, hypercholesterolemia, atherosclerosis, coronary artery disease, congestive heart failure, cardiovascular disease, hypertension, coronary heart disease, angina, pellagra, Hartnup's syndrome, carcinoid syndrome, arterial occlusive disease, obesity, hypothyroidism, vasoconstriction, osteoarthritis, rheumatoid arthritis, diabetes, Alzheimer's disease, lipodystrophy, or dyslipidemia, comprising the step of:

co-administering to a mammal in need thereof a therapeutically effective amount of a compound of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin, simvastatin, gemcabene, and probucol.

A method of treating hyperlipidemia, comprising the step of:

co-administering to a mammal in need thereof a therapeutically effective amount of a compound of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin, simvastatin, gemcabene, and probucol.

A method of raising serum high-density lipoprotein (HDL) levels in a mammal, comprising the step of:

co-administering to a mammal in need thereof a therapeutically effective amount of a compound of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin, simvastatin, gemcabene, and probucol.

A method of lowering serum low-density lipoprotein (LDL) levels in a mammal, comprising the step of:

co-administering to a mammal in need thereof a therapeutically effective amount of a compound of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin, simvastatin, gemcabene, and probucol.

A method of lowering serum lipoprotein (a) (Lp(a)) levels in a mammal, comprising the step of:

co-administering to a mammal in need thereof a therapeutically effective amount of a compound of the present invention; a therapeutically effective amount of niacin; and a therapeutically effective amount of a statin selected from the group consisting of atorvastatin, cerivastatin, fluvastatin, lovastatin, mevastatin, pitavastatin, pravastatin, rosuvastatin, simvastatin, gemcabene, and probucol.

In certain embodiments, the present invention relates to any of the aforementioned methods and the attendant limitations, wherein said statin is lovastatin or atorvastatin.

A method of treating diabetes in a mammal, comprising the step of:

co-administering to a mammal in need thereof a therapeutically effective amount of a compound of the present invention or a pharmaceutically acceptable salt thereof; and a glitazone selected from the group consisting of troglitazone, rosiglitazone, and pioglitazone.

A method of treating diabetes in a mammal, comprising the step of:

co-administering to a mammal in need thereof a therapeutically effective amount of a compound of the present invention or a pharmaceutically acceptable salt thereof; niacin; and a glitazone selected from the group consisting of troglitazone, rosiglitazone, and pioglitazone.

A method of treating diabetes in a mammal, comprising the step of:

co-administering to a mammal in need thereof a therapeutically effective amount of a compound of the present invention or a pharmaceutically acceptable salt thereof; and a fibrate selected from the group consisting of fenofibrate and bezafibrate.

A method of treating diabetes in a mammal, comprising the step of:

co-administering to a mammal in need thereof a therapeutically effective amount of a compound of the present invention or a pharmaceutically acceptable salt thereof; niacin; and a fibrate selected from the group consisting of fenofibrate and bezafibrate.

In certain embodiments, the present invention relates to any of the aforementioned methods and the attendant limitations, wherein said mammal is a primate, bovine, ovine, rodent, equine, canine, or feline.

In certain embodiments, the present invention relates to any of the aforementioned methods and the attendant limitations, wherein said mammal is a human.

In certain embodiments, the present invention relates to any of the aforementioned methods and the attendant limitations, wherein said compound or compounds are administered by inhalation.

In certain embodiments, the present invention relates to any of the aforementioned methods and the attendant limitations, wherein said compound or compounds are administered orally.

In certain embodiments, the present invention relates to any of the aforementioned methods and the attendant limitations, wherein said compound or compounds are administered intravenously.

In certain embodiments, the present invention relates to any of the aforementioned methods and the attendant limitations, wherein said compound or compounds are administered sublingually.

In certain embodiments, the present invention relates to any of the aforementioned methods and the attendant limitations, wherein said compound or compounds are administered ocularly.

In certain embodiments, the present invention relates to any of the aforementioned methods and the attendant limitations, wherein said compound or compounds are administered transdermally.

In certain embodiments, the present invention relates to any of the aforementioned methods and the attendant limitations, wherein said compound or compounds are administered rectally.

In certain embodiments, the present invention relates to any of the aforementioned methods and the attendant limitations, wherein said compound or compounds are administered vaginally.

In certain embodiments, the present invention relates to any of the aforementioned methods and the attendant limitations, wherein said compound or compounds are administered topically.

In certain embodiments, the present invention relates to any of the aforementioned methods and the attendant limitations, wherein said compound or compounds are administered intramuscularly.

In certain embodiments, the present invention relates to any of the aforementioned methods and the attendant limitations, wherein said compound or compounds are administered subcutaneously.

In certain embodiments, the present invention relates to any of the aforementioned methods and the attendant limitations, wherein said compound or compounds are administered buccally.

In certain embodiments, the present invention relates to any of the aforementioned methods and the attendant limitations, wherein said compound or compounds are administered nasally.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251-259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "bicyclo-ring" as used herein refers to a bridged ring system, such as a quinuclidine (shown below).

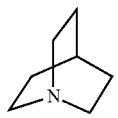

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluoromethyl), cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho (o-), meta (m-) and para (p-) are art-recognized and apply to 1,2-, 1,3- and 1,4-disubstituted benzenes, respectively. For example, the names 1,2-dimethylbenzene, ortho-dimethylbenzene and o-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, fluoroalkyl (such as trifluoromethyl), cyano, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, fluoroalkyl (such as trifluoromethyl), cyano, or the like.

The term "carbocycle" is art recognized and includes an aromatic or non-aromatic ring in which each atom of the ring is carbon. The flowing art-recognized terms have the following meanings: "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2^-$.

The terms "amine" and "amino" are art-recognized and include both unsubstituted and substituted amines, e.g., a moiety that may be represented by the general formulas:

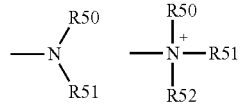

wherein R50, R51 and R52 each independently represent a hydrogen, an alkyl, an alkenyl, $-(CH_2)_m-R61$, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or $-(CH_2)_m-R61$. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

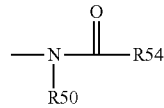

wherein R50 is as defined above, and R54 represents a hydrogen, an alkyl, an alkenyl or $-(CH_2)_m-R61$, where m and R61 are as defined above.

The term "amido" is art recognized as an amino-substituted carbonyl and includes a moiety that may be represented by the general formula:

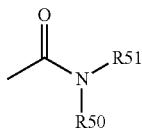

wherein R50 and R51 are as defined above. Certain embodiments of the amide in the present invention will not include amides which may be unstable.

The term "alkylthio" is art recognized and includes an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethylthio, and the like.

The term "carbonyl" is art recognized and includes such moieties as may be represented by the general formulas:

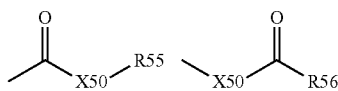

wherein X50 is a bond or represents an oxygen or a sulfur, and R55 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 is not hydrogen, the formula represents an "ester". Where X50 is an oxygen, and R55 is as first defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "oxime" and "oxime ether" are art-recognized and refer to moieties that may be represented by the general formula:

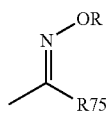

wherein R75 is hydrogen, alkyl, cycloalkyl, alkenyl, alkynyl, aryl, aralkyl, or —$(CH_2)_m$—R61. The moiety is an "oxime" when R represents independently for each occurrence H; and it is an "oxime ether" when R is alkyl, cycloalkyl, alkenyl, alkynyl, aryl, aralkyl, or —$(CH_2)_m$—R61.

The terms "alkoxyl" or "alkoxy" are art recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—R61, where m and R61 are described above.

The term "sulfonate" is art recognized and includes a moiety that may be represented by the general formula:

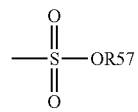

in which R57 is an electron pair, hydrogen, alkyl, cycloalkyl, or aryl.

The term "sulfate" is art recognized and includes a moiety that may be represented by the general formula:

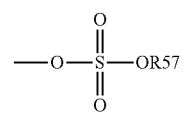

in which R57 is as defined above.

The term "sulfonamido" is art recognized and includes a moiety that may be represented by the general formula:

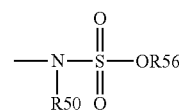

in which R50 and R56 are as defined above.

The term "sulfamoyl" is art-recognized and includes a moiety that may be represented by the general formula:

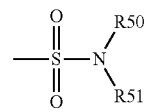

in which R50 and R51 are as defined above.

The term "sulfonyl" is art recognized and includes a moiety that may be represented by the general formula:

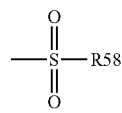

in which R58 is one of the following: hydrogen, alkyl, alkenyl, alkynyl, cycloalkyl, heterocyclyl, aryl or heteroaryl.

The term "sulfoxido" is art recognized and includes a moiety that may be represented by the general formula:

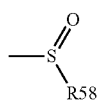

in which R58 is defined above.

The term "phosphoryl" is art-recognized and may in general be represented by the formula:

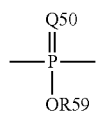

wherein Q50 represents S or O, and R59 represents hydrogen, a lower alkyl or an aryl. When used to substitute, e.g., an alkyl, the phosphoryl group of the phosphorylalkyl may be represented by the general formulas:

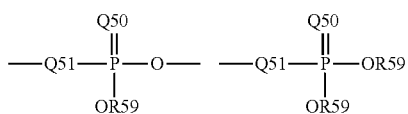

wherein Q50 and R59, each independently, are defined above, and Q51 represents O, S or N. When Q50 is S, the phosphoryl moiety is a "phosphorothioate".

The term "phosphoramidite" is art recognized and includes moieties represented by the general formulas:

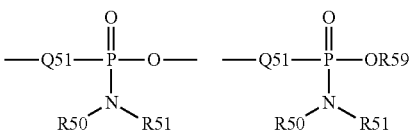

wherein Q51, R50, R51 and R59 are as defined above.

The term "phosphonamidite" is art recognized and includes moieties represented by the general formulas:

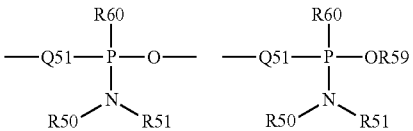

wherein Q51, R50, R51 and R59 are as defined above, and R60 represents a lower alkyl or an aryl.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

For purposes of the invention, the chemical elements are identified in accordance with the Periodic Table of the Elements, CAS version, Handbook of Chemistry and Physics, 67th Ed., 1986-87, inside cover.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled-release agents, such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In some cases, in order to prolong the effect of a drug, it is desirable to slow the absorption of the drug from subcutaneous or intramuscular injection. This result may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers, such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, administration by injection, infusion or inhalation; topical by lotion or ointment; and rectal by suppositories. Oral administrations are preferred.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals, such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Micelles

Microemulsification technology improves bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 Daltons up to about 5,000 or 10,000 Daltons, and more preferably from about 300 Daltons to about 5,000 Daltons. In a particularly preferred embodiment, the polymer is polyethyleneglycol having a molecular weight of from about 100 to about 5,000 Daltons, and more preferably having a molecular weight of from about 300 to about 5,000 Daltons. In a particularly preferred embodiment, the polymer is polyethyleneglycol of 750 Daltons (PEG(750)). Polymers may also be defined by the number of monomers therein; a preferred embodiment of the present invention utilizes polymers of at least about three monomers, such PEG polymers consisting of three monomers (approximately 150 Daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letters alpha, beta and gamma, respectively. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17-beta-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259; incorporated by reference) and Gramera, et al. (U.S. Pat. No. 3,459,731; incorporated by reference) described electroneutral cyclodextrins. Other derivatives include cyclodextrins with cationic properties [Parmeter (II), U.S. Pat. No. 3,453,257; incorporated by reference], insoluble crosslinked cyclodextrins (Solms, U.S. Pat. No. 3,420,788; incorporated by reference), and cyclodextrins with anionic properties [Parmeter (III), U.S. Pat. No. 3,426,011; incorporated by reference]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127; incorporated by reference).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes useful in the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes useful in the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts, such as ammonium sulfate and ammonium chloride, organic acids, such as citric acid, benzoic acid, and ascorbic acid, inorganic bases, such as sodium carbonate, potassium carbonate, calcium carbonate, zinc carbonate, and zinc hydroxide, and organic bases, such as protamine sulfate, spermine, choline, ethanolamine, diethanolamine, and triethanolamine and surfactants, such as Tween® and Pluronic®. Pore forming agents which add microstructure to the matrices (i.e., water soluble compounds, such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of 4-pyridin-3-yl-but-3-enoic acid (Compound 2035)

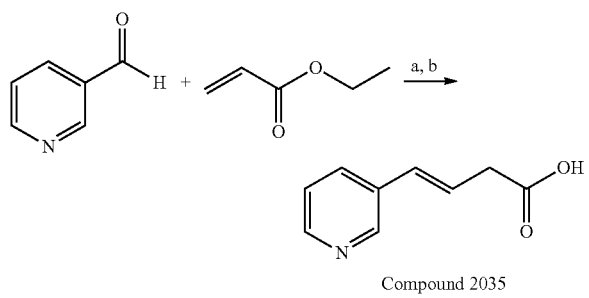

Compound 2035

Reaction conditions: (a) Ethyl acrylate, Ph₃P, n-hexanol, 140° C., 4 hr, 55%; (b): NaOH, MeOH—H₂O, 98%.

The target compound 4-pyridin-3-yl-but-3-enoic acid (Compound 2035) was prepared by two steps starting from the commercial available 3-Pyridinecarboxaldehyde. Reaction of this aldehyde with ethyl acrylate and triphenylphosphine in a sealed tube for 4 hr at 140° C. gave ethyl 4-pyridin-3-yl-3-butenoate in a 55% yield. Kirby, Anthony J.; Walwyn, David R. Effective molarities for intramolecular hydride transfer. Reduction by 1,4-dihydropyridines of the neighboring α-ketoester group. Gazzetta Chimica Italiana (1987), 117 (11), 667-80. This reaction is a self-priming Wittig reaction and the yield was not optimized. Gilbert Stork, R. A. Kretchmer, R. H. Schlessinger. The Stereospecific Total Synthesis of dl-Lycopodine. J. Am. Chem. Soc. (1968), 90, 1647. Hydrolysis of the ester using the routine condition and the subsequent purification with preparative HPLC afforded the target compound 2035 with almost quantitative yield.

Example 2

Synthesis of 4-[6-(2-pyrrolidin-1-yl-ethyl)-pyridin-3-yl]-but-3 enoic acid (Compound 2035B)

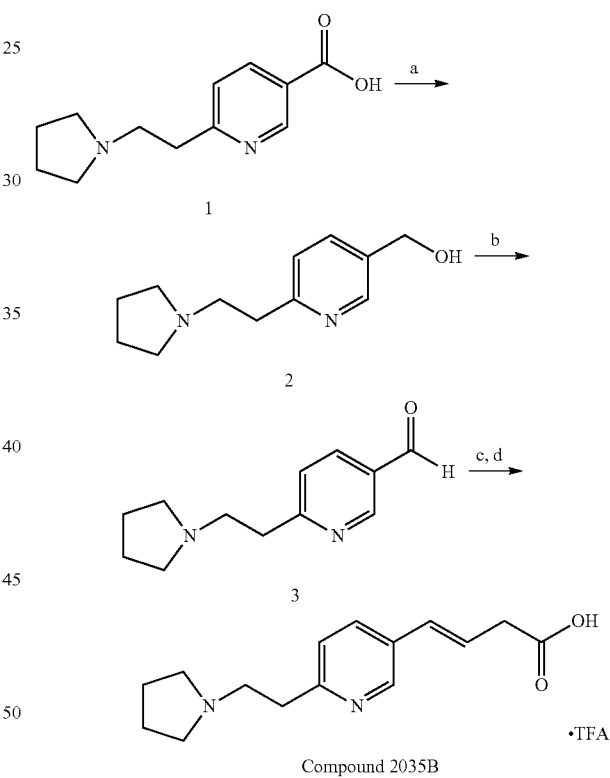

Compound 2035B

Reaction conditions: (a) LiAlH₄, THF, 0° C., 4 hr, 80%; b) MnO₂, CH₂Cl₂, r. t., 18 hr, 60%; c) Ethyl acrylate, Ph₃P, n-hexanol, 140° C., 4 hr; d) NaOH, MeOH—H₂O, 4% yield for the two steps.

The target compound 4-[6-(2-pyrrolidin-1-yl-ethyl)-pyridin-3-yl]-but-3-enoic acid (Compound 2035B) was prepared by four steps starting from the commercial available 6-[2-(Pyrrolidin-1-yl)ethyl]pyridine 1. Firstly, reduction of acid 1 with lithium aluminum hydride was performed in THF at 0° C. for 4 hr, providing alcohol 2 in a yield of 80%. Compound 2 was then oxidized to the corresponding aldehyde 3 using Manganese (IV) oxides as the reagent in a yield of 60%. Delarue, S.; Girault, S.; Maes, L.; Debreu-Fontaine, M.-A.; Labaeid, M.; Grellier, P.; Sergheraert, C. Synthesis and in Vitro and in Vivo Antimalarial Activity of New 4-Anilinoquinolines. *J. Med. Chem.* 2001, 44(17), 2827-2833. Reaction of this aldehyde with ethyl acrylate and triphenylphosphine in a sealed tube for 4 hr at 140° C. gave ethyl 4-[6-(2-pyrrolidin-1-yl-ethyl)-pyridin-3-yl]-but-3-enoic acid, which on subsequent hydrolysis using the routine condition followed by purification with preparative HPLC afforded the target compound 2035B as a TFA salt with a 4% yield. Kirby, Anthony J.; Walwyn, David R. Effective molarities for intramolecular hydride transfer. Reduction by 1,4-dihydropyridines of the neighboring α-ketoester group. Gazzetta Chimica Italiana (1987), 117(11), 667-80. However, the yields were not optimized.

Example 3

Synthesis of Compound 2035C

Reagents: i) ethyl pyruvate; ii) (−)-8-phenylmenthol; iii) L-Selectride; iv) base.

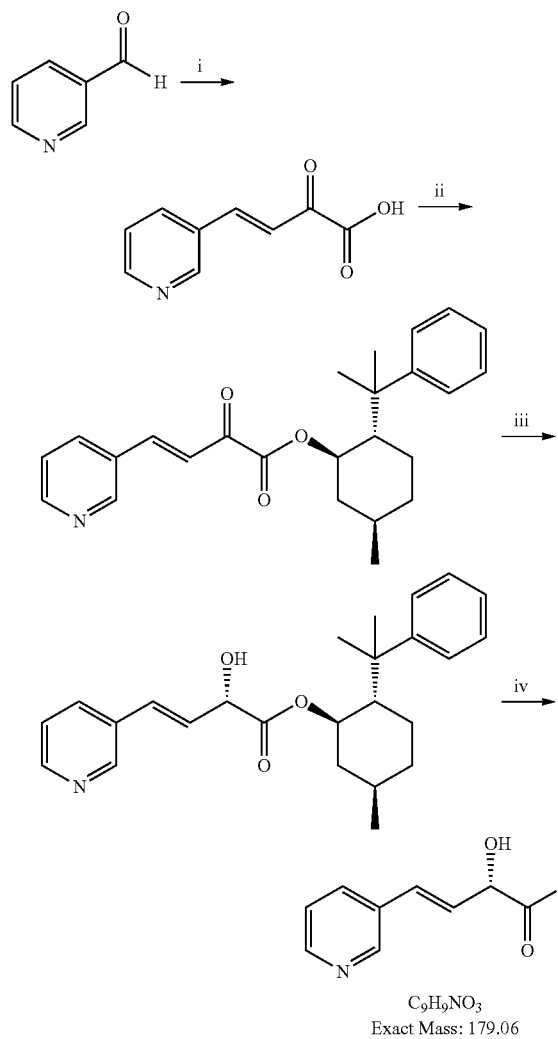

LC/MS data for 2035C—The peak at 7.3 min showed: 180 [M+H].
Gradient: 0-5 min: 0% ACN; 5-15 min: 0-5% ACN; 15-25 min: 5-98% ACN.

Example 4

Synthesis of Compound 2035D

Reagents: i) $Ph_3PCH_2CH_2CO_2H$.

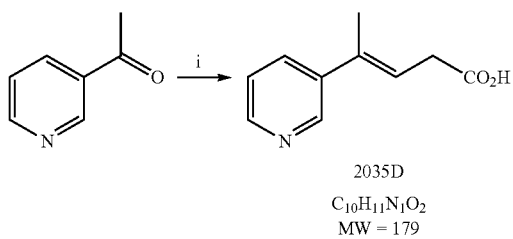

LC/MS data for 2035D—the peak at 17.4 min showed: 178 [M+H].
Gradient: 0-5 min: 2% ACN; 5-20 min: 2-15% ACN; 20-30 min: 15-98% ACN.

Example 5

Synthesis of Compound 2805

Reagents: i) Methaneboronic acid, 16%; ii) Ethyl acrylate; iii) NaOH, 35% yield for the last two steps.

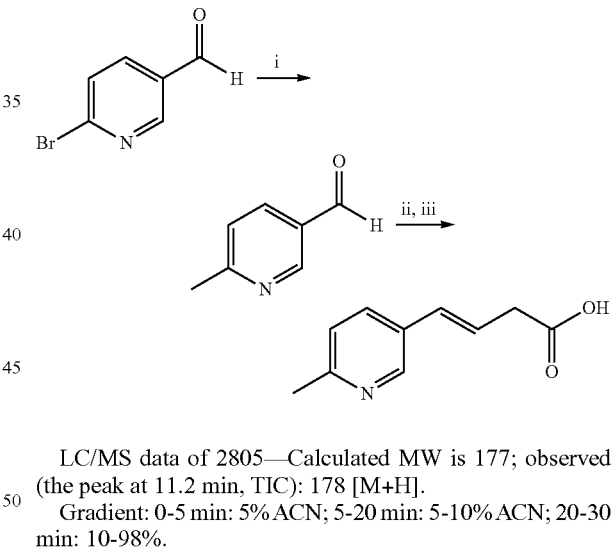

LC/MS data of 2805—Calculated MW is 177; observed (the peak at 11.2 min, TIC): 178 [M+H].
Gradient: 0-5 min: 5% ACN; 5-20 min: 5-10% ACN; 20-30 min: 10-98%.

Example 6

Synthesis of Compound 2805B

Reagents: i) 1-Ethaneboronic acid, 43%; ii) Ethyl acrylate; iii) NaOH, 30% yield for the last two steps.

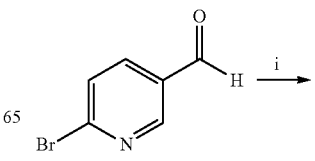

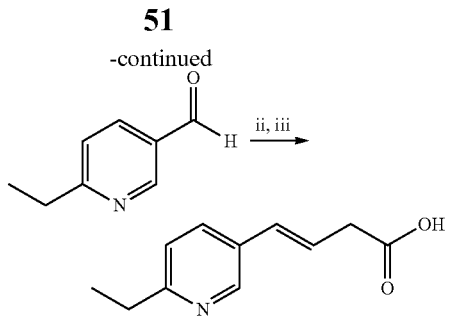

LC/MS data of 2805B—confirmed preparation of target compound.

Gradient: 0-5 min: 5% ACN; 5-20 min: 5-15% ACN; 20-30 min: 15-98% ACN.

Example 7

Synthesis of Compound 2805C

Reagents: i) 1-Propaneboronic acid, 31%; ii) Ethyl acrylate; iii) NaOH, total yield of the two steps was ~24%.

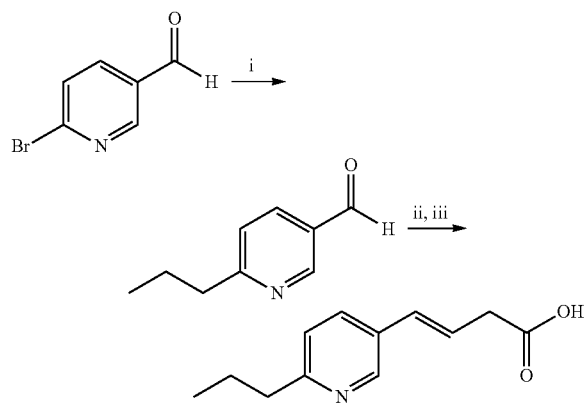

LC/MS data of 2805C—Calculated MW is 205; observed (the peak at 13.4 min, TIC): 206 [M+H]. Gradient: 0-5 min: 10% ACN; 5-20 min: 10-30% ACN.

Example 8

Synthesis of Compound 2805D

Reagents: i) 1-Butaneboronic acid, 55%; ii) Ethyl acrylate; iii) NaOH, total yield of the two steps was ~60%.

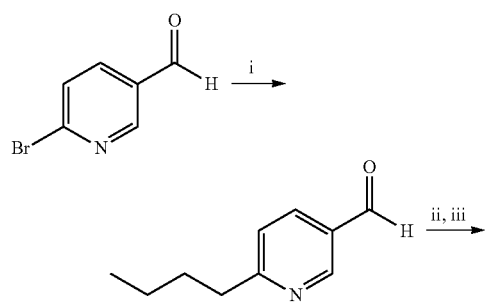

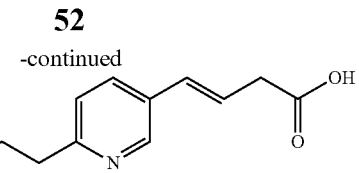

LC/MS data of 2805D—Calculated MW is 219; observed (the peak of 20.9 min): 220 [M+H].

Gradient: 0-5 min: 2% ACN; 5-20 min: 2-30% ACN; 20-35 min: 30-98% ACN.

Example 9

Outline of Hep G 2 Cell Assay Experimental Protocol

Split HepG2 cells in 24 well plates 2~3 days prior to niacin treatment, 0.5 mL complete DMEM media is added per well
Cells were pre-incubated with niacin (1 mM) for 24~48 h
Wash HepG2 cells 3 times with PBS
Incubate HepG2 cells in 250 mL medium C (DMEM containing 5 mg/mL fatty acid free BSA), containing $^{125}$I-labelled HDL (5-10 mg/mL with specificity of 300-500 cpm/ng HDL protein. For 16 h
Aspirate the media and wash the cells with 0.5 mL of 0.1 mg/mL BSA-PBS twice, and with PBS twice
Cells were digested in 250 mL of 1 N NaOH at room temperature overnight
100 mL of cell lysate was used for gamma-counting
100 mL of cell lysate was used for protein assay by BCA method
HDL uptake activity is expressed as "cpm of $^{125}$I-HDL uptake/mg of cell protein.

Example 10

Outline of PGD2 Assay Experimental Protocol

THP-1 cells were grown in RPMI complete media
$2 \times 10^6$ cells/well in 24 well flask were seeded in serum free media containing 16 nM/mL of PMA. Cells were allowed to differentiate into macrophages for 12 hours
The media was replaced with complete RPMI media and incubation continued for 5 hours
After incubation, media was aspirated and cells were treated with niacin and niacin analogs in 1 mL of serum free RPMI media.
Incubated for 30 min. 100 mL of media was collected, PGD2 secreted was derivitized into stable MOX derivative.
PGD2 in the sample was assayed by using PGD2 assay kit from Cayman chemicals.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating hyperlipidemia, obesity, diabetes, or dyslipidemia, comprising the step of:

administering to a mammal in need thereof a therapeutically effective amount of a compound represented by structure A, or a pharmaceutically acceptable salt thereof:

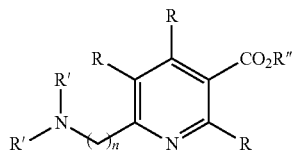

wherein

R represents independently for each occurrence H, alkyl, alkenyl, alkynyl, aryl, heteroaryl, aralkyl, heteroaralkyl, fluoride, chloride, bromide, iodide, nitro, cyano, sulfonic acid, alkylsulfoxyl, arylsulfoxyl, heteroarylsulfoxyl, aralkylsulfoxyl, heteroaralkylsulfoxyl, alkenylsulfoxyl, alkynylsulfoxyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, thiol, alkylthio, arylthio, aralkylthio, heteroaralkylthio, alkenylthio, alkynylthio, formyl, acyl, formyloxy, acyloxy, formylthio, acylthio, amino, alkylamino, arylamino, heteroarylamino, aralkylamino, heteroaralkylamino, alkenylamino, alkynylamino, formylamino, acylamino, carboxylate, alkyloxycarbonyl, aryloxycarbonyl, heteroaryloxycarbonyl, aralkyloxycarbonyl, heteroaralkyloxycarbonyl, carboxamido, alkylaminocarbonyl, arylaminocarbonyl, heteroarylaminocarbonyl, aralkylaminocarbonyl, or heteroaralkylaminocarbonyl;

R' represents independently for each occurrence H, alkyl, alkenyl, alkynyl, aryl, heteroaryl, aralkyl, heteroaralkyl, alkylsulfonyl, arylsulfonyl, heteroarylsulfonyl, aralkylsulfonyl, heteroaralkylsulfonyl, alkenylsulfonyl, alkynylsulfonyl, hydroxyl, alkoxyl, aryloxyl, heteroaryloxyl, aralkyloxy, heteroaralkyloxy, alkenyloxy, alkynyloxy, formyl, acyl, amino, alkylamino, arylamino, heteroarylamino, aralkylamino, heteroaralkylamino, alkenylamino, alkynylamino, formylamino, acylamino, alkyloxycarbonyl, aryloxycarbonyl, heteroaryloxycarbonyl, aralkyloxycarbonyl, heteroaralkyloxycarbonyl, alkylaminocarbonyl, arylaminocarbonyl, heteroarylaminocarbonyl, aralkylaminocarbonyl, or heteroaralkylaminocarbonyl; or the two instances of R' taken together represent —$(CH_2)_2$—, —$(CH_2)_3$—, —$(CH_2)_4$—, —$(CH_2)_5$—, or —$(CH_2)_6$—;

R" represents independently for each occurrence H, alkyl, alkenyl, alkynyl, aryl, heteroaryl, aralkyl, or heteroaralkyl; and n is 1, 2, 3, or 4.

2. The method of claim 1, wherein R represents independently for each occurrence H, fluoride, chloride, cyano, methyl, or ethyl.

3. The method of claim 1, wherein R represents independently for each occurrence H.

4. The method of claim 1, wherein R' represents independently for each occurrence H, alkyl, alkenyl, alkynyl, aryl, heteroaryl, aralkyl, or heteroaralkyl; or the two instances of R' taken together represent —$(CH_2)_2$—, —$(CH_2)_3$—, —$(CH_2)_4$—, —$(CH_2)_5$—, or —$(CH_2)_6$—.

5. The method of claim 1, wherein the two instances of R' taken together represent —$(CH_2)_2$—, —$(CH_2)_3$—, —$(CH_2)_4$—, —$(CH_2)_5$—, or —$(CH_2)_6$—.

6. The method of claim 1, wherein the two instances of R' taken together represent —$(CH_2)_4$—.

7. The method of claim 1, wherein R" represents H, alkyl, aryl, or aralkyl.

8. The method of claim 1, wherein R" represents H.

9. The method of claim 1, wherein n is 2.

10. The method of claim 1, wherein R represents independently for each occurrence H; and n is 2.

11. The method of claim 1, wherein R represents independently for each occurrence H; and the two instances of R' taken together represent —$(CH_2)_4$—.

12. The method of claim 1, wherein R represents independently for each occurrence H; and R" represents H or alkyl.

13. The method of claim 1, wherein the two instances of R' taken together represent —$(CH_2)_4$—; and n is 2.

14. The method of claim 1, wherein R represents independently for each occurrence H; the two instances of R' taken together represent —$(CH_2)_4$—; and n is 2.

15. The method of claim 1, wherein R represents independently for each occurrence H; R" represents H or alkyl; and n is 2.

16. The method of claim 1, wherein R represents independently for each occurrence H; the two instances of R' taken together represent —$(CH_2)_4$—; and R" represents H or alkyl.

17. The method of claim 1, wherein R represents independently for each occurrence H; the two instances of R' taken together represent —$(CH_2)_4$—; R" represents H or alkyl; and n is 2.

18. The method of claim 1, wherein R represents independently for each occurrence H; the two instances of R' taken together represent —$(CH_2)_4$—; R" represents H; and n is 2.

19. The method of claim 1, wherein the compound is selected from the group consisting of:

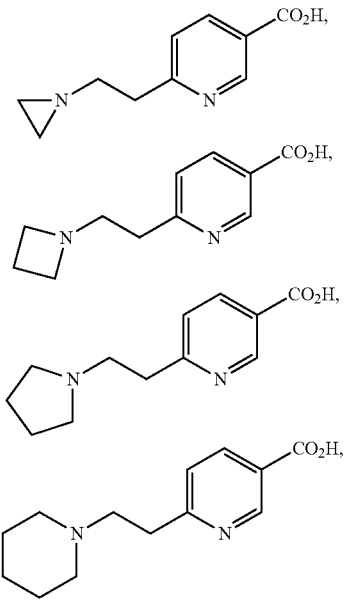

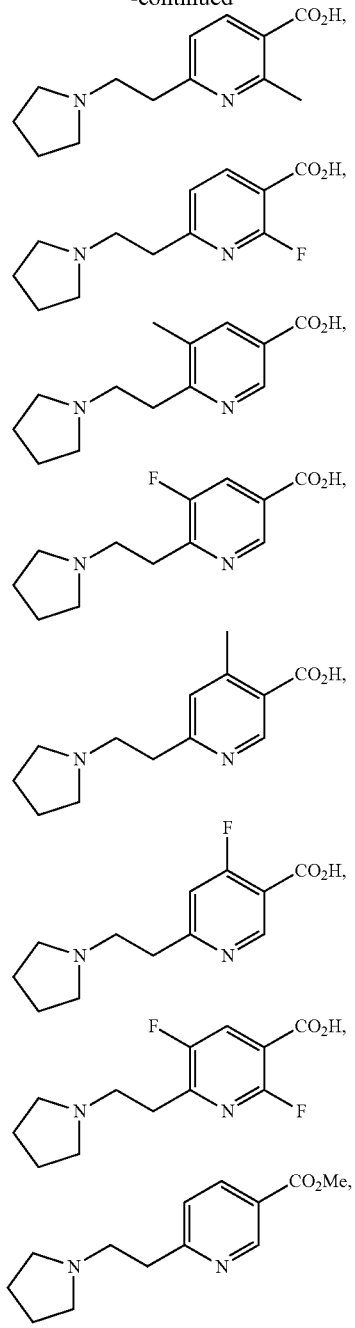
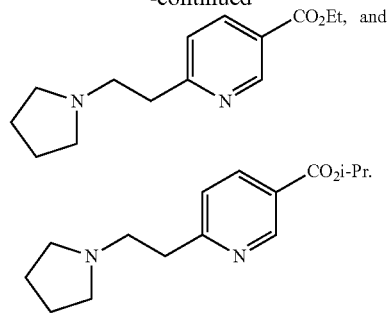

20. The method of claim 1, wherein the mammal is a human.

21. The method of claim 20, further comprising the step of:
co-administering to a mammal in need thereof a therapeutically effective amount of a statin selected from the group consisting of atorvastatin, cerivastatin, fluvastatin, lovastatin, mevastatin, pitavastatin, pravastatin, rosuvastatin, and simvastatin.

22. The method of claim 20, wherein said method treats hyperlipidemia or dyslipidemia.

23. The method of claim 1, wherein said method treats hyperlipidemia.

24. The method of claim 1, wherein said method treats obesity.

25. The method of claim 1, wherein said method treats diabetes.

26. The method of claim 1, wherein said method treats dyslipidemia.

27. The method of claim 18, wherein said method treats hyperlipidemia.

28. The method of claim 27, wherein the mammal is a human.

29. The method of claim 18, wherein said method treats obesity.

30. The method of claim 29, wherein the mammal is a human.

31. The method of claim 18, wherein said method treats diabetes.

32. The method of claim 31, wherein the mammal is a human.

33. The method of claim 18, wherein said method treats dyslipidemia.

34. The method of claim 32, wherein the mammal is a human.

* * * * *